United States Patent [19]

Williams et al.

[11] Patent Number: 5,131,907

[45] Date of Patent: * Jul. 21, 1992

[54] METHOD OF TREATING A SYNTHETIC NATURALLY OCCURRING SURFACE WITH A COLLAGEN LAMINATE TO SUPPORT MICROVASCULAR ENDOTHELIAL CELL GROWTH, AND THE SURFACE ITSELF

[75] Inventors: Stuart K. Williams, Wilmington, Del.; Bruce E. Jarrell, Philadelphia, Pa.

[73] Assignee: Thomas Jefferson University, Philadelphia, Pa.

[*] Notice: The portion of the term of this patent subsequent to Apr. 11, 2006 has been disclaimed.

[21] Appl. No.: 666,475

[22] Filed: Mar. 6, 1991

Related U.S. Application Data

[63] Continuation of Ser. No. 848,453, Apr. 4, 1986, abandoned, which is a continuation-in-part of Ser. No. 742,086, Jun. 6, 1985, Pat. No. 4,820,626.

[51] Int. Cl.$^5$ ............ A61F 2/04; A61F 2/02; B05D 3/06; C12N 5/06
[52] U.S. Cl. ............................ 600/36; 623/1; 427/40; 427/41; 424/93; 435/1; 435/240.7; 435/240.241
[58] Field of Search ............ 435/240.241; 623/1; 424/93; 427/40, 41; 600/36

[56] References Cited

U.S. PATENT DOCUMENTS

| | | | |
|---|---|---|---|
| 4,276,448 | 10/1966 | Kronenthal | 128/334 |
| 4,632,842 | 12/1986 | Karwoski et al. | 427/2 |
| 4,656,083 | 4/1987 | Hoffman et al. | 428/422 |
| 4,687,482 | 8/1987 | Hanson | 623/9 |
| 4,795,459 | 1/1989 | Jauregul | 435/180 |
| 4,820,626 | 4/1989 | Williams et al. | 435/1 |
| 4,927,676 | 5/1990 | Williams | 428/36 |

FOREIGN PATENT DOCUMENTS 8303536 10/1983 PCT Int'l Appl. .

OTHER PUBLICATIONS

Nichols et al 1981, Trans. Am. Soc. Artif. Intern. Organs. XXVII, 208–212.

Meenaghan, J. Biomed. Mater. Res. 13(4) pp. 631–644 (1979), Biol. Abst. 68:71423.

T. A. Belden, et al, "Endothelial Cell Seeding of Small-Diameter Vascular Grafts", Transactions American Society for Artificial Internal Organs, vol. 28, (Apr. 14–16) pp. 173–184 (1982).

Abedin, M. Z. et al, "Collagen Heterogeneity and Its Functional Significance", *Die Angewandte Mark-*

(List continued on next page.)

*Primary Examiner*—Robert A. Wax
*Assistant Examiner*—Christopher S. F. Low
*Attorney, Agent, or Firm*—Woodcock Washburn Kurtz Mackiewicz & Norris

[57] ABSTRACT

A novel implantable prosthesis for implantation in human patients is disclosed which comprises a synthetic substrate and a Type IV/V collagen surface layer seeded with a confluent monolayer of autologous endothelial cells. In the preferred embodiment, a base layer of interstitial collagen is adhered to the substrate. The Type IV/V collagen surface layer is provided in a laminate comprising an intermediate layer of interstitial collagen which is covalently bound to the aforementioned base layer. A cross linking agent, such as glutaraldehyde, is utilized to covalently bind the interstitial collagen base layer to the substrate, and the collagen intermediate layer to the base layer. The cross linking agent is subsequently deactivated with a soluble peptide, such as lysine. Autologous endothelial cells, such as microvascular endothelial cells derived from adipose tissue, are then seeded at high densities on the pretreated graft material. Those cells adhere in suitable percentage within times compatible with most vascular surgical procedures, and, even more importantly, flatten on that surface to assume the appearance of a natural, cobblestone morphology. The subject surface is resistant to shear stress, and yields good results when tested as a vena cava implant in a dog.

10 Claims, 9 Drawing Sheets

OTHER PUBLICATIONS

*romolekulare chemie*, vol. 111, No. 1701 Jan., 1983, pp. 107-122.

W. E. Burkel, "The Development of Cellular Linings in Artificial Vascular Protheses", *Biocompatible Polymers, Metal, and Composites* edited by M. Szycher (1983) pp. 165-178.

Baker et al., "Endothelialization of Human Collagen Surfaces with Human Adult Endothelial Cells" *Amer. J. Surgery*, 150:197-200 (1985).

Cardiovascular Physiology, by Robert M. Berne and Matthew N. Levy, C. V. Mosby Company (1981).

Peter W. Rose, et al. "Gas plasma technology and surface treatment of polymers prior to adhesive bonding", *Plastics 85*, Proceeding of the SPE 43rd Annual Technial Conference and Exhibition pp. 685-688 (1985).

Jarrell et al, "Human Adult Endothelial Cell Growth in Culture", *Journal of Vascular Surgery*, vol. 1, No. 6, pp. 757-764 (Nov., 1984).

Herring et al, "A Single-Staged Technique for Seeding Vascular Grafts with Autogenous Endothelium", *Surgery*, 84(4):498-504 (1978).

Graham et al, "Cultured Autogenous Endothelial Cell Seeding of Prosthetic Vascular Grafts", *Surg. Forum*, 30:204-206 (1979).

Graham et al, "Expanded Polytetrafluoroethylene Vascular Prostheses Seed with Enzymatically Derived and Cultured Canine Endothelial Cells", *Surgery*, 91:550-559 (1982).

Dilley et al, "Endothelial Seeding of Vascular Prostheses" *Biology of Endothelial Cells*, Jaffe Ed., The Hague: Martinus Nijhoff, pp. 401-411, (1984).

Berger et al, "Healing of Arterial Prostheses in Man: Its Incompleteness", *Ann. Surg.* 175:118-127 (1972).

Jaffe et al, "Culture of Human Endothelial Cells Derived From Umbilical Veins", *J. Clin. Invest.*, 52:2745-56 (1973).

Sharefkin et al, "Early Normalization of Platelet Survival by Endothelial Seeding of Dacron Arterial Prosthesis in Dogs", *Surgery*, 92:385-398 (1982).

Stanley et al, "Enhanced Patency of Small Diameter Externally Supported Dacron Iliofemoral Grafts Seeded with Endothelial Cells", *Surgery*, 92:994-1005 (1982).

Watkins et al, "Adult Human Saphenous Vein Endothelial Cells: Assessment of Their Reproductive Capacity for Use in Endothelial Seeding of Vascular Prostheses", *J. Surg. Res.*, 36:588-596 (1984).

Sauvage et al, "Interspecies Healing of Porous Arterial Prostheses", *Arch. Surg.* 109:698-705 (1974).

Fishman, "Endothelium: A Distributed Organ of Diverse Capabilities", *Annals of New York Academy of Sciences*, pp. 1-8 (1982).

F. Hess et al, "The Endothelialization Process of a Fibrous Polyurethane Microvascular Prosthesis After Implantation in the Abdominal Aorta of the Rat", *Journal of Cardiovascular Surgery*, vol. 24, No. 5, pp. 515-524 (Sep.-Oct. 1983).

T. A. Belden et al, "Endothelial Cell Seeding of Small-Diameter Vascular Grafts", *Trans. Am. Soc. Artif. Intern. Organs*, 28:173-177, (1982).

W. K. Nicholas et al, "Increased Adherence of Vascular Endothelial Cells to Biomer Precoated with Extracellular Matrix", *Trans. Am. Soc. Artif. Intern. Organs*, 28:208-212 (1981).

C. L. Ives et al, "The Importance of Cell Origin and Substrate in the Kinetics of Endothelial Cell Alignment in Response to Steady Flow", *Trans. Am. Soc. Artif. Inter. Organs*, 29:269-274 (1983).

S. G. Eskin et al, "Behavior of Endothelial Cells Cultured on Silastic and Dacron Velour Under Flow Conditions *In Vitro*: Implications for Prelining Vascular Grafts with Cells", *Artificial Organs*, 7(1):31-37 (1983).

W. E. Burkel et al, "Fate of Knitted Dacron Velour Vascular Grafts Seeded with Enzymatically Derived Autlogous Canine Endothelium", *Trans. Am. Soc. Artif. Intern. Organs*, 28:178-182 (1982).

M. B. Herring et al, "Seeding Arterial Prostheses with Vascular Endothelium", *Ann. Surg.*, vol. 190, No. 1, pp. 84-90, (Jul., 1979).

A. Wesolow, "The Healing of Arterial Prostheses—The State of the Art", *Thorac. Cardiovasc. Surgeon*, 30:196-208 (1982).

T. Ishihara et al, "Occurrence and Significance of Endothelial Cells in Implanted Porcine Bioprosthetic Valves", *American Journal of Cardiology*, 48:443-445 (Sep., 1981).

Wagner et al, "Exclusion of Albumin from Vesicular Ingestion by Isolated Microvessels", *Microvascular Research*, 19:127-130 (1980).

Williams et al, "Metabolic Studies on the Micropinocytic Process in Endothelial Cells", *Microvascular Research*, 18:175–184 (1979).

Williams, "Vesicular Transport of Proteins by Capillary Endothelium", *Annals of the New York Academy of Sciences*, pp. 457–467 (1983).

Williams et al, "Enhanced Vesicular Injestion of Nonenzymatically Glucosylated Proteins by Capillary Endothelium", *Microvascular Research*, 28:311–321 (1984).

Williams et al, "Endocytosis and Exocytosis of Protein in Capillary Endothelium", *Journal of Cellular Physiology*, 120:157–162 (1984).

Williams et al, "Isolated and Characterization of Brain Endothelial Cells: Morphology and Enzyme Activity", [Journal of Neurochemistry, 35:374 $\propto$ 381 (1980).

Williams et al, "Micropinocytic Ingestion of Glycosylated Albumin by Isolated Microvessels: Possible Role in Patho-Genesis of Diabetic Microangiopathy", *Proc. Natl. Acad. Sci. USA*, vol. 79, No. 4, pp. 2393–2397, Apr., 1981.

Williams et al, "Regulation of Micropinocytosis in Capillary Endothelium by Multivalent Cations", *Microvascular Research*, 21:175–182 (1981).

Williams et al, "Quantitative Determination of Deoxyribonucleic Acid from Cells Collected on Filters", *Analytical Biochemistry*, 107:17–20 (1980).

McDonagh et al, "The Preparation and Use of Fluorescent-Protein Conjugates for Microvascular Research", *Micro-Vascular Research*, 27:14–27 (1984).

Madri et al, "Capillary Endothelial Cell Cultures: Phenotypic Modulation by Matrix Components", *Journal of Cell Biology*, vol. 97, pp. 153–165, Jul. 1983.

Williams et al, "Adult Human Endothelial Cell Compatibility with Prosthetic Graft Material", *Journal of Surgical Research*, 38:618–629 (1985).

Kern et al, "Isolation and Culture of Microvascular Endothelium from Human Adipose Tissue": *J. Clin. Invest.*, 71:1822–1829 (Jun., 1983).

van Wachem ete al, "Interaction of Cultured Human Endothelial Cells with Polymeric Surfaces of Different Wettabilities", *Biomaterials* 6:403–408 (1985).

Azizkhan et al, "Mast Cell Heparin Stimulates Migration of Capillary Endothelial Cell in Vitro", *J. Exp. Med.*, vol. 152, pp. 931–944, (Oct., 1980).

Roblin, et al., "Cell Surface Changes Correlated With Density Dependent Growth Inhibition. Glycosaminoglycan Metabolism In 3T3, SV3T3, and Con A Selected Revertant Cells", *Biochemistry* vol. 14, No. 2, pp. 347–357 (1975).

Yang, et al., "The Effect of Heparin On Growth Of Mammalian Cells in vitro (40290)", *Proceedings on the Soc. For Experimental Biology and Medicine*, 159:88–93 (1978).

Thornton, et al., "Human Endothelial Cells: Use of Heparin in Cloning and Long-Term Serial Cultivation", *Science* vol. 222, pp. 623–625 (Nov. 11, 1983).

Laterra et al., "Functions for Fibronectin, Hyaluronate, and Heparin Proteglycans in Substratum Adhesion of Fibroblasts", *Extracellular Matrix*, pp. 197–207 (1982).

Maciag, et al., "Serial Propagation of Human Endothelial Cells in vitro", *Journal of Cell Biology*, 91:420–426 (1981).

Maciag, et al., "An Endothelial Cell Growth Factor From Bovine Hypothalamus: Identification and Partial Characterization", *Proc. Natl. Acad. Sci. USA*, 76:5674–5678 (1979).

Madri, "The Immunochemistry Of Extracellular Matrix", Boca Raton, Fla. CRC Press, vol. 1, pp. 75–90 (1982).

Liotta, et al., "New Method For Preparing Large Surfaces Of Intact Human Basement membrane For Tumor Invasion Studies", *Cancer Letters*, 11:141–152 (1980).

Baker, et al., "Endothelialization Of Human Collagen Surfaces With Human Adult Endothelial Cells", *American Journal Of Surgery*, 150:197–200 (Aug. 1985).

Glassberg, et al., "Cultured Endothelial Cells Derived From Human Iliac Arteries", In Vitro,18:859–866 (1982).

Maciag, et al., "Factors Which Stimulate The Growth Of Human Umbilical Vein Endothelial Cells in vitro", *Biology of Endothelial Cells*, Jaffe, E. A. (ed) Martinus Nijhoff pp. 87–96 (1984).

Jaffe, et al., "Synthesis of Aantihemophilia Factor Antigen By Cultured Human Endothelial Cells", *J. Clin Invest.* 55:2757–64 (1973).

Lewis, "Endothelium In Tissue Culture", *Am. J. Anat.*, 30:39–59 (1922).

Williams, et al., "Isolation And Culture Of Phenotypically Diverse Human Perinephric Fat Capillary Endothelium", *Microvascular Research*, 29:260 (1985).

Radomski, et al, "Initial Adherence Of Human Capillary Endothelial Cells To Dacron", Abstract presented Nov. 21, 1985, Association For Academic Surgery.

Jarrell, et al., "Use Of Freshly Isolated Capillary Endothelial Cells For The Immediate Establishment Of A Monolayer On A Vascular Graft At Surgery". Abstract presented Feb. 13, 1986. Society for University Surgeons.

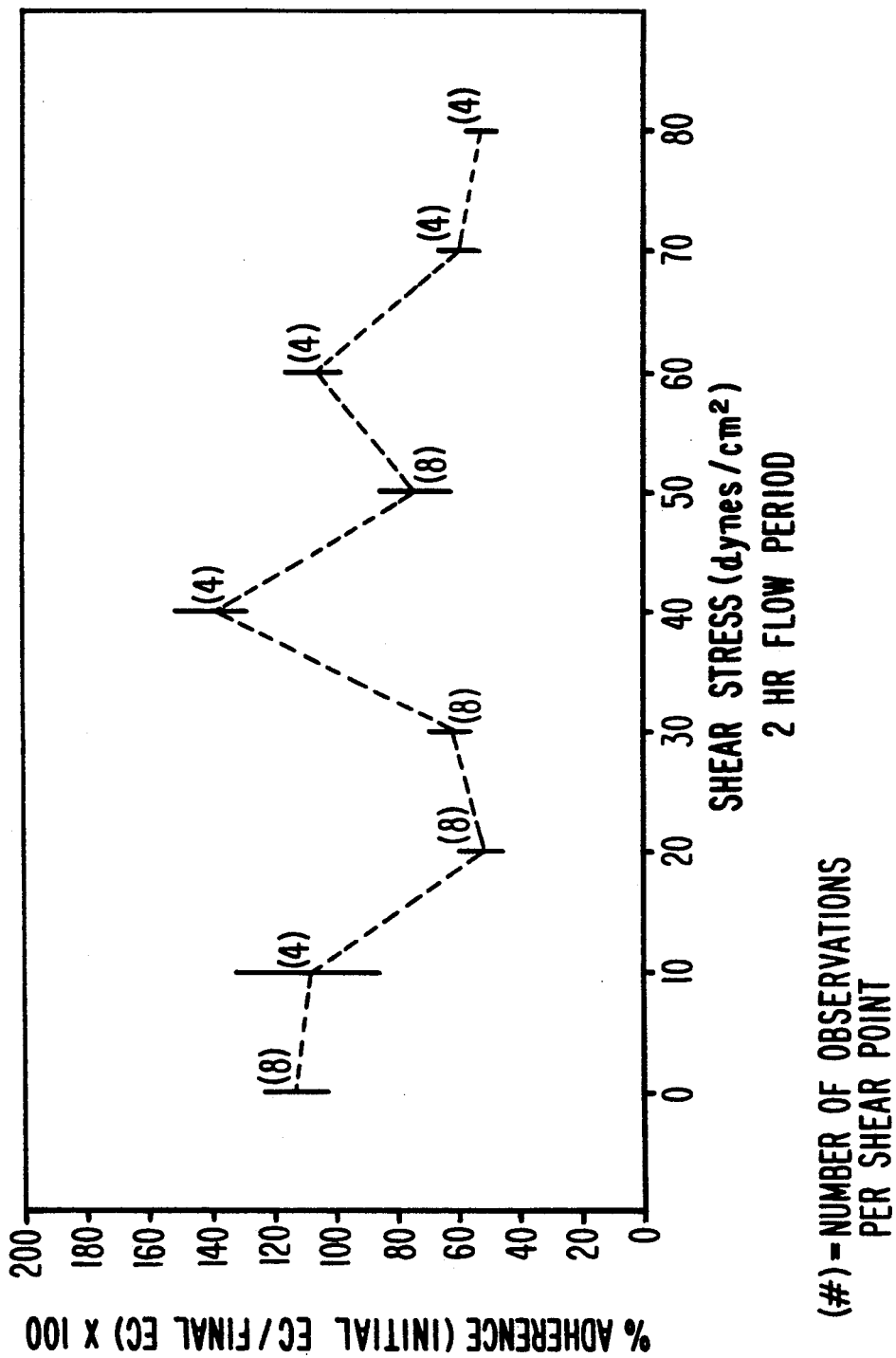

METHOD OF TREATING A SYNTHETIC NATURALLY OCCURRING SURFACE WITH A COLLAGEN LAMINATE TO SUPPORT MICROVASCULAR ENDOTHELIAL CELL GROWTH, AND THE SURFACE ITSELF

CROSS-REFERENCE TO RELATED APPLICATIONS

This is a continuation of application Ser. No. 848,453, filed Apr. 4, 1986, now abandoned, which is a continuation-in-part of our prior U.S. Pat. No. 4,820,626 Ser. No. 742,086, filed Jun. 6, 1985 entitled "A Method of Treating a Synthetic or Naturally. Occurring Surface with Microvascular Endothelial Cells and the Treated Surface Itself", which is assigned to the assignee of the present application and which is hereby incorporated by reference as if fully set forth herein.

This application is also related to copending application Ser. No. 210,218, filed Jun. 17, 1988 which is now U.S. Pat. No. 4,994,387 a continuation of Ser. No. 099,241, filed Sep. 21, 1987 now abandoned, which is a continuation of applications Ser. Nos. 848,913 and 848,917, both filed Apr. 7, 1986 both now abandoned, which respectively, are continuations of applications Ser. Nos. 550,305 and 550,306, respectively, both filed Nov. 19, 1983, now both abandoned, a portion of which is assigned to the assignee hereof, which application is hereby incorporated by reference as if fully set forth herein.

BACKGROUND OF THE INVENTION

The present invention relates to the field of implantable prosthetic devices for implantation into humans, and more particularly to synthetic implants such as vascular grafts which are now commonly used to replace the large veins or arteries of human patients. It further relates to treatments provided to such grafts to improve endothelial cell adhesion and/or proliferation thereon.

The development of the idea of prosthetic vascular grafts has been a major goal of vascular surgery since the first grafts were used over 30 years ago. Most approaches have concentrated on creating a surface that is thromboresistant, with the majority of these efforts directed toward an improved polymer surface. Perhaps the ideal blood-surface interface is the naturally occurring human endothelium. If present on a prosthetic graft, it would offer many of the advantages of a native vessel. Unfortunately, endothelialization occurs only to a limited degree in prosthetic grafts when placed into humans, in contrast to animals where graft endothelialization does occur. Seeding endothelial cells onto preclotted prosthetic grafts prior to implantation has improved the endothelial cell coverage of grafts in animals, but this technique has had limited use in humans. See "Human Adult Endothelial Cell Growth in Culture", Bruce Jarrell et al, *Journal of Vascular Surgery*, Vol 1, No. 6, pp. 757-764 (November, 1984); Herring et al, "A Single and Staged Technique for Seeding Vascular Grafts with Autogenous Endothelium", *Surgery*, 1978, 84:498-504; Graham et al, "Cultured Autogenous Endothelial Cell Seeding of Vascular Prosthetic Grafts", *Surg Forum* 30:204-6 (1979); Graham et al, "Expanded Polytetrafluoroethylene Vascular Prostheses Seeded with Enzymatically Derived and Cultured Canine Endothelial Cells", *Surgery* 91:550-9 (1982) and Dilley et al, "Endothelial Seeding of Vascular Prostheses", Jaffe ed *Biology of Endothelial Cells*, The Hague: Martinus Nijhoff, 1984 pp 401-11.

Over the past three decades artificial grafts have been used to provide immediate restoration of blood flow to areas of ischemia as a result of atherosclerotic vascular disease. In addition, they have been used to provide vascular access for hemodialysis in patients with chronic renal failure, and in the repair of arterial aneurysms. Although initially successful at restoring perfusion to ischemic tissues, the long-term prognosis for these grafts is not encouraging. Over an extended period, grafts less than 4 mm in diameter lose their patency as they become occluded via fibrin deposttion and cellular adhesion. Dilley supra. This process appears to be secondary, and to be due in part to the thrombogenic nature of the nude (i.e, non-endothelialized) surface of the implanted prostheses. See Berger et al, "Healing of Arterial Prostheses in Man: It's Incompleteness", *Ann. Surg.* 175:118-27 (1972). Thus, much current research is being aimed at either: (1) developing grafts with an artificial, non-thrombogenic surface, or (2) lining vascular prostheses with human endothelial cells, in the hope of producing a non-thrombogenic endothelial cell surface such as exists in native human vessels.

Endothelial cells from animal sources have been studied in culture since the 1920's In 1973 Jaffe et al, successfully cultured endothelial cells from human umbilical veins and these cells have been characterized functionally. See Jaffe et al, "Synthesis of Antihemophilia Factor Antigen by Cultured Human Endothelial Cells", *J. Clin. Invest.* 55:2757-64 (1973); and Lewis, "Endothelium in Tissue Culture", *Am. J. Anat.* 30:39-59 (1922); Jaffe et al, "Culture of Human Endothelial Cells Derived From Umbilical Veins", *J. Clin. Invest.* 52:2745-56 (1973). These cell cultures demonstrate a growth potential, but the total number of cells produced from a single umbilical vein is usually quite limited, in the range of a 10-100-fold increase in harvested endothelial cells.

While several techniques have been proposed to increase the number of cells produced in the use of human umbilical vein endothelial cells, the ability to culture endothelial cells in large numbers remains less than ideal. Some investigators have had some success in culturing human adult endothelial cells from pulmonary arteries and veins, but only for short periods of time. It has also been shown that human iliac artery endothelial cells may be cultured for a short number of passages. In a study by Glassberg et al, for example, it is reported that 50 to 500 viable cells can be obtained per 5-inch vessel segment, a very low yield. "Cultured Endothelial Cells Derived From Human Iliac Arteries", In Vitro 18:859-66 (1982). Fry et al have reported successfully culturing human adult endothelial cells from abdominal arteries removed at the time of cadaver donor nephrectomy, but these cells also demonstrated limited proliferative capacity.

It is apparent from existing techniques that it is difficult to produce enough cells to preendothelialize a graft with a reasonable amount of vessel from the donor patient. Rather than completely endothelializing a graft prior to implantation, the concept of subconfluent "seeding" of a preclotted graft developed. Seeding vascular grafts with autogenous endothelial cells has recently been shown to increase the rate of endothelial coverage of the grafts of experimental animals. See Herring et al and Graham et al supra. Once covered by endothelium, grafts in dogs have been shown to be less thrombogenic as measured by platelet re-activity, to be more resistant to inoculation from blood-born bacterial challenge, and to have prolonged patency of small-caliber vascular grafts. See Sharefkin et al, "Early Normalization of Platelet Survival by Endothelial Seeding of Dacron Arterial Prostheses in Dogs", *Surgery* 92:385-93 (1982); Stanley et al, "Enhanced Patency of Small Diameter Externally Supported Dacron Iliofemoral Grafts Seeded with Endothelial Cells", *Surgery* 92:994-1005 (1982); and Watkins et al, "Adult Human Saphenous Vein Endothelial Cells: Assessment of Their Reproductive Capacity for Use in Endothelial Seeding of Vascular Prostheses", *J. Surg. Res.* 36:588-96 (1984).

A point of major concern when translating to human graft seeding has been the ability to produce enough endothelial cells with the use of human vascular tissue to allow seeding at a density high enough to attain endothelial coverage of the graft. Watkins et al, using human saphenous vein remnants following coronary artery bypass surgery were able to produce small quantities of endothelial cells in culture, and reported a 100-fold increase in confluent cell area obtained in culture after 4 to 6 weeks. See Watkins et al supra.

Even if it were possible to substantially expand the number of endothelial cells available through vigorous culturing techniques, concerns would still remain concerning the "health" of these endothelial cells after as many as 40 or 50 population doublings. Furthermore, the incubation of such cells in cultures which are foreign to their natural environment raises further concerns about genetic alterations and/or patient contamination with viruses, toxins or other damaging materials.

Many endothelialization procedures are suggested in the literature. Investigations in this area have been complicated by the diverse nature of the endothelium itself, and by the species to species differences which have been found relating to the behavior and characteristics of the endothelium. Fishman, "Endothelium: A Distributed Organ of Diverse Capabilities", *Annals of New York Academy of Sciences*, pp. 1-8 (1982); Sauvage et al, "Interspecies Healing of Porous Arterial Prostheses", *Arch Surg.* 109:698-705 (1974); and Berger, "Healing of Arterial Prostheses in Man: Its Incompleteness", supra. Nonetheless, the literature is replete with reports of experiments involving the seeding of endothelial cells on various grafts, in various species, with a mixture of results. F. Hess et al, "The Endothelialization Process of a Fibrous Polyurethane Microvascular Prostheses After Implantation in the Abdominal Aorta of the Rat", *Journal of Cardiovascular Surgery*, Vol. 24, No. 5, pp. 516-524 (September-October, 1983); W. K. Nicholas et al, "Increased Adherence of Vascular Endothelial Cells to Biomer Precoated with Extracellular Matrix", *Trans. Am. Soc. Artif. Intern Organs*, 28:208-212 (1981); C. L. Ives et al, "The Importance of Cell Origin and Substrate in the Kinetics of Endothelial Cell Alignment in Response to Steady Flow", *Trans. Am. Soc. Artif. Inten Organs*, 29:269-274 (1983); L. M. Graham et al, "Expanded Polytetrafluoroethylene Vascular Prostheses Seeded with Enzymatically Derived and Cultured Canine Endothelial Cells", *Surgery*, Vol 91, No. 5, pp. 550-559 (1982); S. G. Eskin et al, "Behavior of Endothelial Cells Cultured on Silastic and Dacron Velour Under Flow Conditions In Vitro: Implications for Prelining Vascular Grafts with Cells", *Artificial Organs*, 7(1):31-37 (1983);T. A. Belden et al, "Endothelial Cell Seeding of Small-Diameter Vascular Grafts", *Trans. Am. Soc. Artif. Intern. Organs*, 28:173-177, (1982); W. E. Burkel et al, "Fate of Knitted Dacron Velour Vascular Grafts Seeded with Enzymatically Derived Autologous Canine Endothelium", *Trans. Am. Soc. Artif. Intern. Organs*, 28:178-182 (1982); M. T. Watkins et al, "Adult Human Saphenous Vein Endothelial Cells: Assessment of Their Reproductive Capacity for Use in Endothelial Seeding of Vascular Prostheses", *Journal of Surgical Research*, 36:588-596 (1984); M. B. Herring et al, "Seeding Arterial Prostheses with Vascular Endothelium", *Ann. Surg.*, Vol. 190, No. 1, pp. 84-90 (July, 1979); A. Wesolow, "The Healing of Arterial Prostheses—The State of the Art", *Thorac. Cardiovasc. Surgeon*, 30:196-208 (1982); T. Ishihara et al, "Occurrence and Significance of Endothelial Cells in Implanted Porcine Bioprosthetic Valves", *American Journal of Cardiology*, 48:443-454 (September, 1981); W. E. Burkel et al, "Fate of Knitted Dacron Velour Vascular Grafts Seeded with Enzymatically Derived Autologous Canine Endothelium", *Trans. Am. Soc. Artif Intern Organ*, 28:178-182 (1982).

A number of papers coauthored by coinventor Stuart Williams relate to the isolation and functioning of rat microvessel endothelial cells, including such cells derived from various tissue sources including epididymal fat. These publications include *Proc. Natl. Acad. Sci. USA*, 78(4):2393-2397 (1981); *Microvascular Research*, 21:175-182 (1981); *Anal. Biochemistry*, 107:17-20 (1980); *Microvascular Research*, 19:127-130 (1980); *Microvascular Research*, 18:175-184 (1979); *Annals of the New York Academy of Sciences*, 457-467 (1983); *Microvascular Research*, 28:311-321 (1984); *Journal of Cellular Physiology*, 120:157-162 (1984); and *Journal of Neurochemistry*, 35(2):374-381 (1980). See also *Microvascular Research*, 27:14-27 (1984) relating to the preparation and use of fluorescent-protein conjugates for microvascular research.

Kern et al report on the isolation of human microvascular endothelial cells, and indicate they may be cultured and used in functional studies. Kern et al, *J. Clin. Invest.*, 71:1822-1829 (1983).

Madri and Williams, "Capillary Endothelial Cells Cultures: Phenotypic Modulation by Matrix Components", *Journal of Cell Biology*, 97:153-165 (1983) discloses the isolation and culture of capillary endothelial cells from rat epididymal fat in media conditioned by bovine aortic endothelial cells and substrata consisting of interstitial or basement membrane collagens, including Types I/III and IV/V collagens. The paper teaches that when cells are grown on interstitial collagens they undergo proliferation, forming a continuous cell layer and, if cultured for long periods of time, form occasional tube like structures. It further discloses that when these cells are grown on basement membrane collagens, they do not proliferate but do aggregate and form tube like structures at early culture times.

Williams et al, "Adult Human Endothelial Cell Compatibility with Prosthetic Graft Material", *Journal of Surgical Research*, 38:618-629 (1985) is also of interest. An Abstract of the subject paper was distributed at the annual meeting of the Association for Academic Surgery, Oct. 31-Nov. 3, 1984. The paper itself was submitted to the editorial board of the Association at that meeting, eventually appearing on or about August of 1985. This Williams et al paper reports the effects of coating with extracellular matrix (Type I/III collagen), fibronectin or plasma, of prosthetic graft material. The highest density of adherence was observed on collagen-coated Dacron grafts, and was equal to the cell density observed in confluent monolayers of HAEC grown on gelatin-coated culture plastic.

Jarrell et al, "Human Adult Endothelial Cell Growth in Culture", *Journal of Vascular Surgery*, 1(6):757-764 (November, 1984) contains a disclosure similar to that of the cross-referenced application which is incorporated by reference in the present application. Note is further taken of the discussion with coinventor Jarrell appearing at pages 762-764 relating to the endothelial cells of capillaries in fat.

A number of publications disclose seeding techniques using grafts which have been pretreated with fibronectin, plasma, or collagen. Eskin et al, "Behavior of Endothelial Cells Cultured on Silastic and Dacron Velour Under Flow Conditions In Vitro: Implications for Prelining Vascular Grafts with Cells" *Artificial Organs*, 7(1):31-37 (1983) discloses tests of tissue-cultured bovine aortic endothelial cells subjected to flow in an in vitro circulatory loop designed to stimulate the flow and pressure conditions in the aorta. Eskin et al explain that endothelial cells cultured on biomaterial substrates are nonthrombogenic when implanted as blood-contacting surfaces, but that this technique has not yet proved feasible for clinical use because the two surgical procedures required (one for cell harvest, and second for cell implantation, with an intervening period for in vitro cell growth) and because the cells, cultured in a stationary environment, are at least partly removed when they are exposed to the flowing blood. Eskin et al cite "more recent studies", with grafts preclotted with blood containing freshly harvested autologous endothelial cells showing greater patency than those preclotted with blood alone. This is said to demonstrate that cell harvesting and implantation can be done in one operation, without an intervening period for culturing the cells, making clinical use of the technique feasible as a means of producing a nonthrombogenic surface.

In "Adult Human Saphenous Vein Endothelial Cells: Assessment of their Reproductive Capacity for Use in Endothelial Seeding of Vascular Prostheses", by Watkins et al, *Journal of Surgical Research*, 36:588-596 (1984), autogenous endothelial seeding of vascular prostheses using venous endothelial cells is reported as reducing platelet-prostheses interactions and improving patency rates in small caliber prostheses in dogs. While the data from dog trials is said to suggest that autogenous endothelial seeding might help human patients, a number of drawbacks to the procedure are discussed, including the availability of large lengths of peripheral veins, variations in different lots of crude collagenase used for the procedure, and the absence of required evidence that the growth capacity of venous endothelial cells was great enough to do autogenous endothelial seeding with endothelial cells from only a small fraction of the available peripheral veins. The tests conducted suggest that the growth potential of adult human saphaneous vein endothelial cells is "theoretically adequate for either immediate interoperative autogenous endothelial seeding or for preimplantation growth of endothelial cell linings on vascular prostheses by culture methods". While the results are said to satisfy one condition for human trial, the authors conclude that "for several reasons they are not sufficient to show that such a trial would succeed."

In recent years, attention has focused upon the poor results generally obtained with small diameter vascular grafts. Such grafts, generally characterized as having internal diameters of less than or equal to 4 mm are generally not used. van Wachem et al, "Interaction of Cultured Human Endothelial Cells with Polymeic Surfaces of Different Wettabilities", *Biomaterials*, 6:403-408 (November, 1985) report that the success of synthetic polymer grafts having relatively large interdiameters (greater than or equal to 4 mm) is achieved in spite of a biological lining created which is "hardly nonthrombogenic". High blood flow and anticoagulant therapy are suggested as preventing occlusion due to further thrombosis formation on the graft surface, notwithstanding the fact that such large diameter grafts are usually preclotted with blood to prevent leakage, leaving a rather thrombogenic surface. Clinical results with small diameter grafts are said to be "disappointing", mainly because of "immediate occlusion of the grafts". In dogs, seeding of endothelial cells onto both large and small diameter grafts have been shown to result in a complete endothelial lining between one and four months. Since vascular endothelium is said to represent a unique non-thrombogenic surface, endothelial cells are reported to be "the first logical choice for lining small diameter vascular grafts". A systematic study of the interaction of endothelial cells and polymers with different surface properties is hypothesized as being able to lead to the "development of grafts which promote overgrowth of endothelial cells". In this regard, van Wachem et al have considered the surface wettability of certain materials which are said to influence adhesion and proliferation of different types of mammalian cells, cell adhesion occurring preferentially to water wettable surfaces. When serum is present in the culture medium, cell adhesion to wettable substrates is suggested as being influenced by the adsorption of serum proteins into the substrates. If cell adhesion is studied in serum-free medium, the adsorption of proteins originating from the cells on to wettable substrates may be of importance.

van Wachem et al note that endothelial cells can be cultured on glass and wettable tissue culture polystyrene, which is a glow discharge treated polystyrene. Wachem et al thus report and suggest the examination of the adhesion and proliferation of human endothelial cells on a number of polymers with different wettabilities in culture medium containing serum.

In addition to the above-cited articles, see also Hess et al, "The Endothelialization Process of a Fibrous Polyurethane Microvascular Prosthesis After Implantation in the Abdominal Aorta of the Rat", *Journal of Cardiovascular Surgery*, 24(5):516-524 (1983), reporting the production of completely endothelialized prostheses at day 21 using a fibrous microvascular polyurethane prosthesis.

The following publications are of particular interest for their disclosures relating to endothelial cell culturing techniques. Azizkhan et al is of interest for its disclosure relating to in vitro bovine capillary endothelial cells and their migratory response to a factor released from mast cells. Roblin et al and Yang et al are of interest for their disclosures of factors effecting the growth of certain mammalian cell cultures. Thorton et al is of interest for its disclosure of the effect of heparin on human endothelial cell growth involving the culturing of human umbilical vein endothelial cells. Thorton et al teach that the described procedures for serial subcultivation can increase the yield of HUVE cells by $10^8$-fold and of adult vessel endothelial cells by $10^{12}$-fold over previously published methods. This is said to permit minimal amounts of human vascular tissue to be used for the generation of large numbers of cultured endothelial cells, thus permitting problems of human pathology involving the endothelium to be approached directly by means of a human endothelial cell model. In addition, the cell system is described as proving valuable for various clinical applications, such as in vitro testing of vasoactive agents and a coating of artificial graft materials. Laterra et al is of interest for its disclosure of functions for fibronectin hyaluronate, and heparin proteoglycans in substratum adhesion of fibroblasts. Maciag et al (1979) is of interest for its description of a human endothelial-cell mytogen obtained from extracts of bovine hypothalamus prepared at neutral pH. The neural-derived endothelial-cell growth factor (ECGF) is said to have the ability to stimulate quiescent human umbilical vein endothelial cells to grow in culture. The addition of ECGF to low seed-density cultures of HUV endothelial cells in fetal bovine serum is said to result in significant increases in endothelial cell growth as compared to that achieved in serum alone. Maciag et al (1981) describes growth of human umbilical vein endothelial cells on a fibronectin matrix in medium 199 supplemented with fetal bovine serum and endothelial cell growth factor. Thus, these publications and the disclosure in the cross-referenced related application, show the state of the art concerning efforts made to culture human endothelial cells, particularly large vessel human endothelial cells such as human umbilical vein endothelial cells (HUEC).

Notwithstanding the work reported in this field, a need still exists for a simple reliable procedure which can successfully endothelialize the surfaces of human implants, such as the surfaces of vascular grafts.

SUMMARY OF THE INVENTION

This invention provides a novel method of treating an implant intended for implantation in a human patient, comprising the steps of providing a synthetic substrate material and treating that material with Type IV/V collagen to improve human endothelial cell adhesion, proliferation and morphology. In the preferred embodiment, such endothelial cells are derived from the human microvascular endothelial cell rich tissue of that patient, which is separated from that tissue and applied to the Type IV/V collagen surface of that implant to provide at least about 50% or greater confluence of said cells on the surface of said implant to be treated. The invention thus provides an implant having a bound Type IV/V collagen surface layer which is well adapted to promote the adhesion and proliferation of the patient's microvascular endothelial cells when seeded at high densities shortly prior to implantation.

The preferred implant comprises a synthetic substrate, one or more immediate layers of Type I/III collagen and a Type IV/V collagen surface layer. The subject graft thus comprises a substrate onto which is applied a laminate comprising at least Type IV/V collagen top surface and a Type I/III collagen underlayer. This collagen laminate is acellular laminate preferably derived from human amnion. The preferred implant is prepared as follows. A synthetic substrate such as polymeric (Dacron) substrate is treated using a glow discharge plasma cleaner to prepare the graft surface for collagen coating. The glow discharge plasma created by this device etches the graft surface and creates a stronger association between the collagen and the graft. The surface of this graft is then treated with a mixture of collagen I and/or III prepared from bovine, or preferably human, sources using conventional procedures, such as those reported in Madri, "The Immunochemistry of Extracellular Matrix", Boca Raton, Fla., CRC Press, (1982) Vol. 1:75-90. The resulting collagen is separated from contaminating proteins by its solubility in acetic acid, and separated from other matrix proteins by its differential solubility in high sodium chloride concentrations. The graft substrate is then treated with the aforementioned solution of collagen still dissolved in acetic acid and the collagen is polymerized on the surface and within the graft by raising the pH of the solution with the addition of a neutral buffer. At 37° C. a gel of collagen forms, which is then crosslinked with glutaraldehyde. This stabilizes the gel and additionally creates an aldehyde activated surface.

The graft is then ready to receive a collagen laminate which is derived from human amnion. This amnion is derived from human placentae prepared in accordance with procedures of Liotta et al, *Cancer Letters*, 11:141-152 (1980). The amnion is physically pulled away from the chorion and chemically treated. The amnionic epithelial cells are then physically stripped away from the amnion surface leaving acellular material with basement membrane collagen (Types IV/V) on one side and interstitial collagen (Types I/III) on the other. The amnion is soaked in phosphate buffered saline before its application to the aforementioned treated graft material.

The prepared collagen laminate is subsequently placed on the aldehyde activated surface of the graft material, with its collagen I/III towards the graft. The amnion layer surface is permitted to interact and bind covalently. Any remaining free aldehyde groups are then inactivated by treating the graft with an amine, amino acid or a peptide with an aldehyde active amine group. Lysine is presently preferred due to its solubility in phosphate buffered saline. The basement membrane surface of the amnion is now oriented away from the graft and can be subsequently treated with human microvascular endothelial cells to create a monolayer. The resulting graft may be sterilized by irradiation or other suitable techniques and stored until needed for use. Its Type IV/V collagen surface is ready to receive a high density seeding of endothelial cells. Such seeding leads to the rapid (within 2 hour) formation of a shear resistant endothelial cell monolayer which exhibits a cobblestone morphology of natural appearance.

A graft prepared in accordance with the present procedures has been placed in a dog to replace the vena cava. Under normal circumstances, an untreated graft will always exhibit rapid clot formation, and will frequently occlude. A significant percentage, perhaps a majority of such dogs die from such grafts, often within twenty minutes of implantation. In the animal tested, the vena cava prepared in accordance with the herein described techniques was removed after two days and showed no signs inconsistent with indefinite patency.

Applicants recognize that human microvascular endothelial cells, that is, the cells which are derived from capillaries, arterioles, and venules, will function suitably in place of large vessel cells even though there are morphological and functional differences between large vessel endothelial cells and microvascular endothelial cells in their native tissues. Moreover, microvascular endothelial cells are present in an abundant supply in body tissue, most notably in fat tissue, and may be used to establish a degree of pre-implantation confluence (i.e., at least 50% confluence) which should dramatically improve the prognosis of most implants. For purposes of further description, fat tissue is designated as the exemplary source of microvascular endothelial cells, but it is to be recognized that endothelial cells from other tissue sources may be used as well.

A vascular graft or other implant is treated to confluence using microvascular endothelial cells which are separated from fat which is obtained at the beginning of an uninterrupted surgical procedure. Fat tissue is removed from the patient after sterile conditions have been established. Microvascular endothelial cells in that fat are then quickly separated from their related tissue by enzymatic digestion and centrifugation, and are used to treat a surface which is then implanted in the patient during the latter stages of the same operation. This procedure obviates any need to culture adult endothelial cells to increase their numbers, and permits a patient to receive a graft which has been treated up to or above confluence with his own fresh, "healthy" endothelial cells.

In accordance with the preferred embodiment of the present invention, the microvascular rich tissue obtained is perinephric fat, subcutaneous fat, omentum, or fat associated with the thoracic or peritoneal cavity. This tissue is then subjected to digestion using a proteolytic enzyme, such as a collagenase comprising caseanase and trypsin, which is incubated with the tissue until the tissue mass disperses to produce a tissue digest. The microvascular endothelial cells are then separated from the digest using low speed centrifugation to produce an endothelial cell rich pellet. The pellet is washed with a buffered saline solution, and may be further purified using a continuous gradient centrifugation process or by use of selective sieving. The resulting microvascular endothelial cells are then preferably suspended in a buffered saline solution containing plasma protein, preferably about 1% plasma protein. This suspension, which comprises, on a volumetric basis, a pellet to solution ratio of 1:5 to 1:15, or preferably about 1:10, is then used to treat the surface by incubating cells with that surface until sufficient adherence of the microvascular endothelial cells to that surface occurs to provide at least 50% confluence. As a result, an improved graft or implant is provided having endothelialized surfaces which are either confluent, or which will reach confluence quite rapidly (within one population doubling) following implantation.

Although the initial percentages of endothelial cell adherence are not generally as high using prostheses having Type IV/V surface layers, the morphology of the resulting endothelial cell layer is far superior to that obtainable using other prosthetic surfaces and/or surface pretreatments. The use of microvascular endothelial cells thus allows for higher density seeding to compensate for lower adhesive yield.

Accordingly, a primary object of the present invention is the provision of a process for improving endothelial cell coverage of vascular grafts and other implants.

A further object of the present invention is the provision of an improved synthetic or naturally occurring implant or graft, particularly an improved vascular graft, which may be endothelialized with microvascular endothelial cells.

These and other objects of the present invention will become apparent from the following, more detailed description.

BRIEF DESCRIPTION OF THE DRAWINGS

FIG. 8 is a graph of microvessel endothelial cells that were seeded onto plasma treated Dacron showing those remaining permanently adherent to grafts following exposure to a wide range of shear rates. Freshly isolated microvessel endothelial cells were seeded onto plasma coated Dacron for 1 hour. After a brief wash, the grafts were exposed to flow conditions for 2 hours using culture medium as the perfusate. Endothelial cells remaining on the graft were counted and compared to control grafts that were identically seeded but not exposed to flow. Statistical evaluation using linear regression analysis revealed $y = 91 - 0.33x$ with a r—value of $-0.26$.

DESCRIPTION OF THE PREFERRED EMBODIMENT

Figure 1:
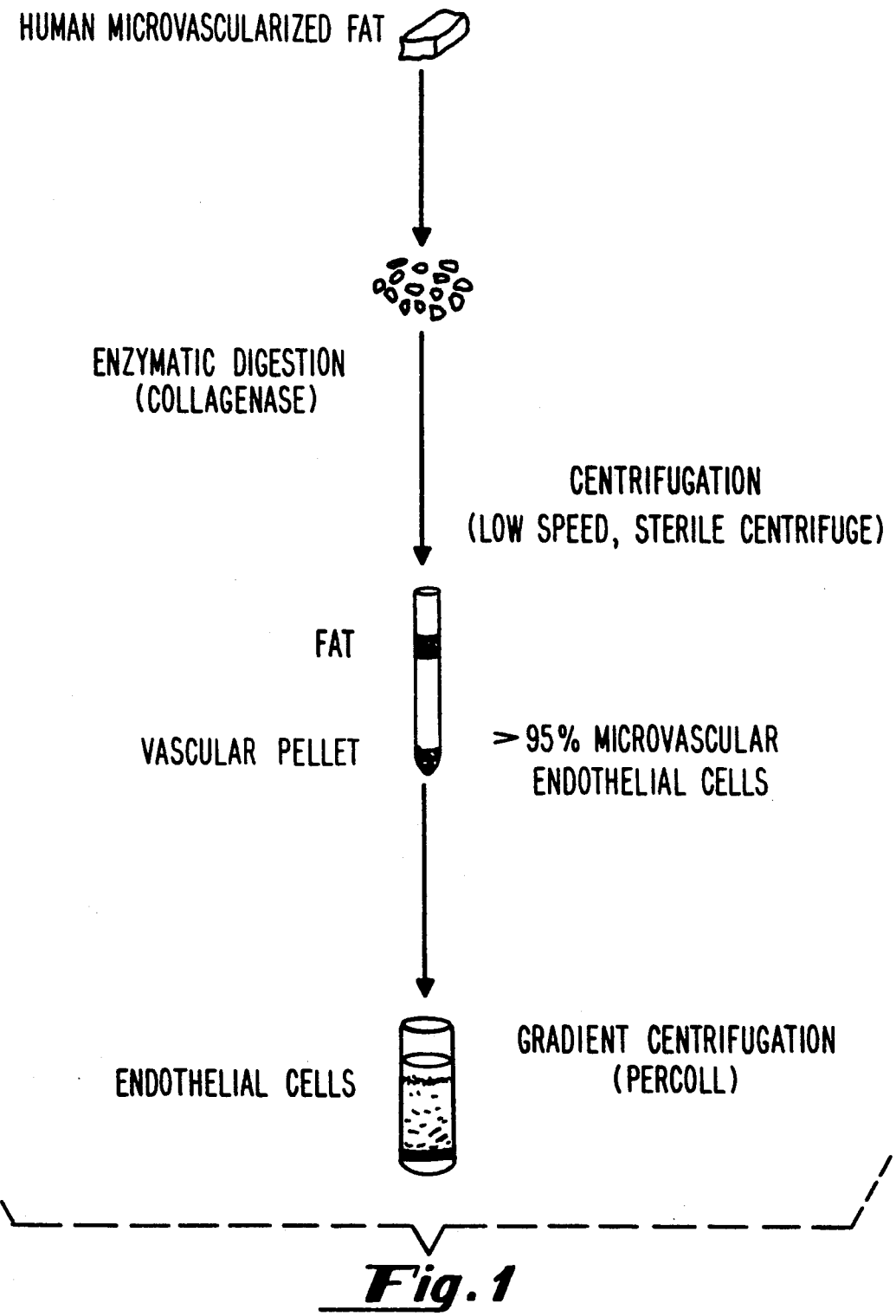
FIG. 1 is a diagram representing the steps followed to obtain human microvascular endothelial cells for use in accordance with the present invention, FIGS. 2(A and B) are graphs illustrating the adherence of thymidine labelled human adult endothelial cells (HAEC) to untreated (FIG. 2A) and platelet rich plasma treated (FIG. 2B) Dacron polyester grafts over a period of 24 hours from the time of seeding.
Figure 2A:
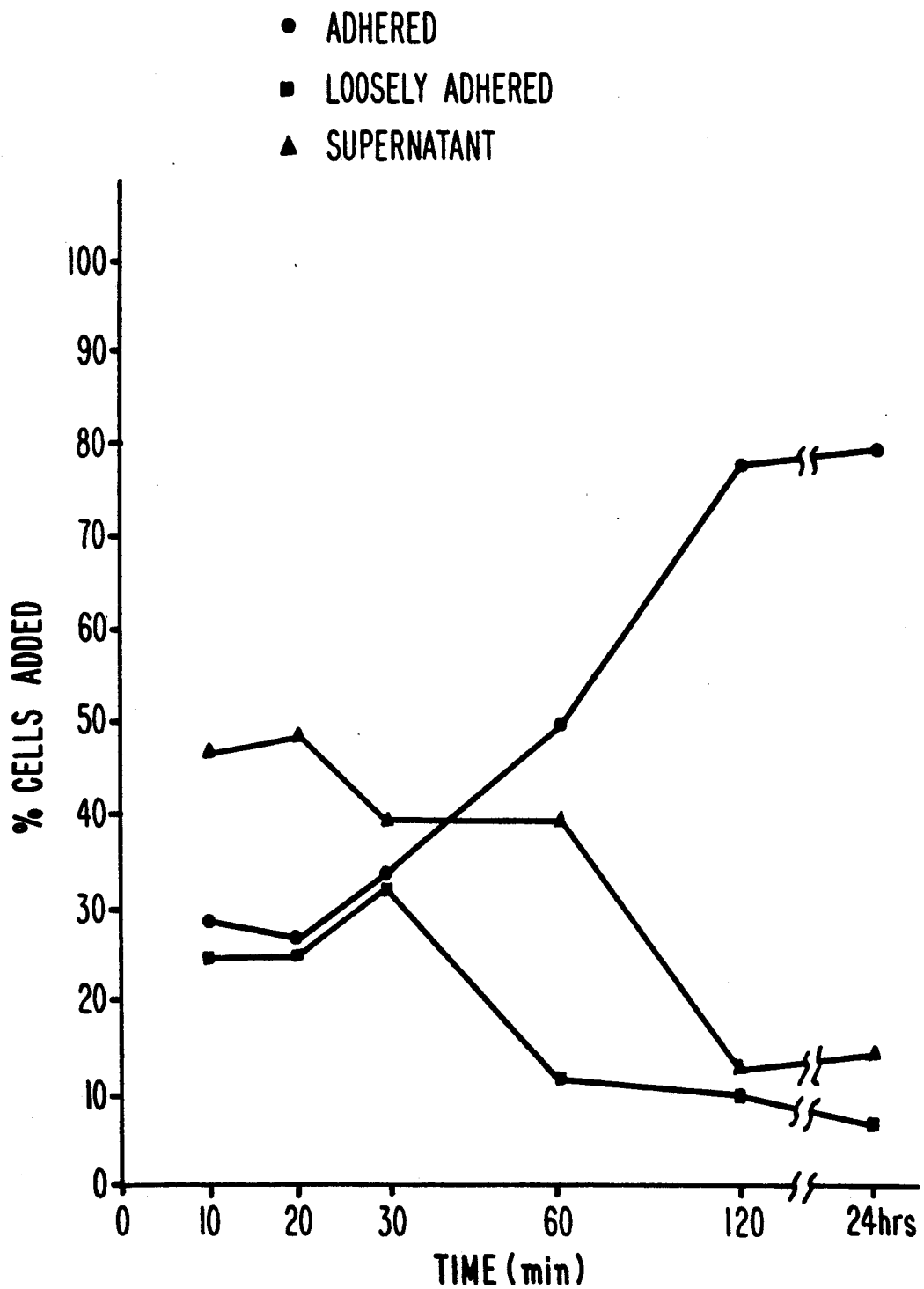
Figure 2B:
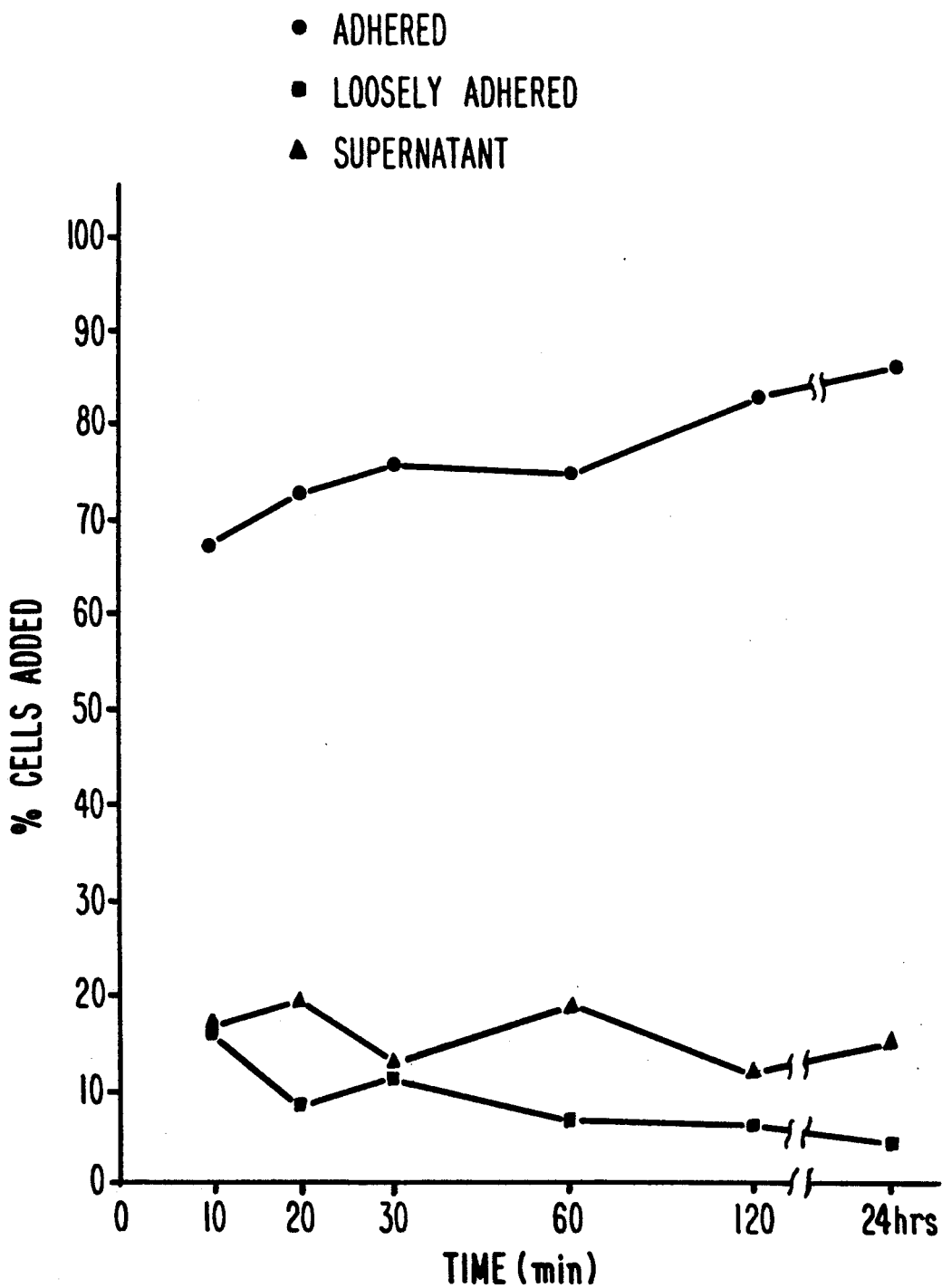
Figure 3:
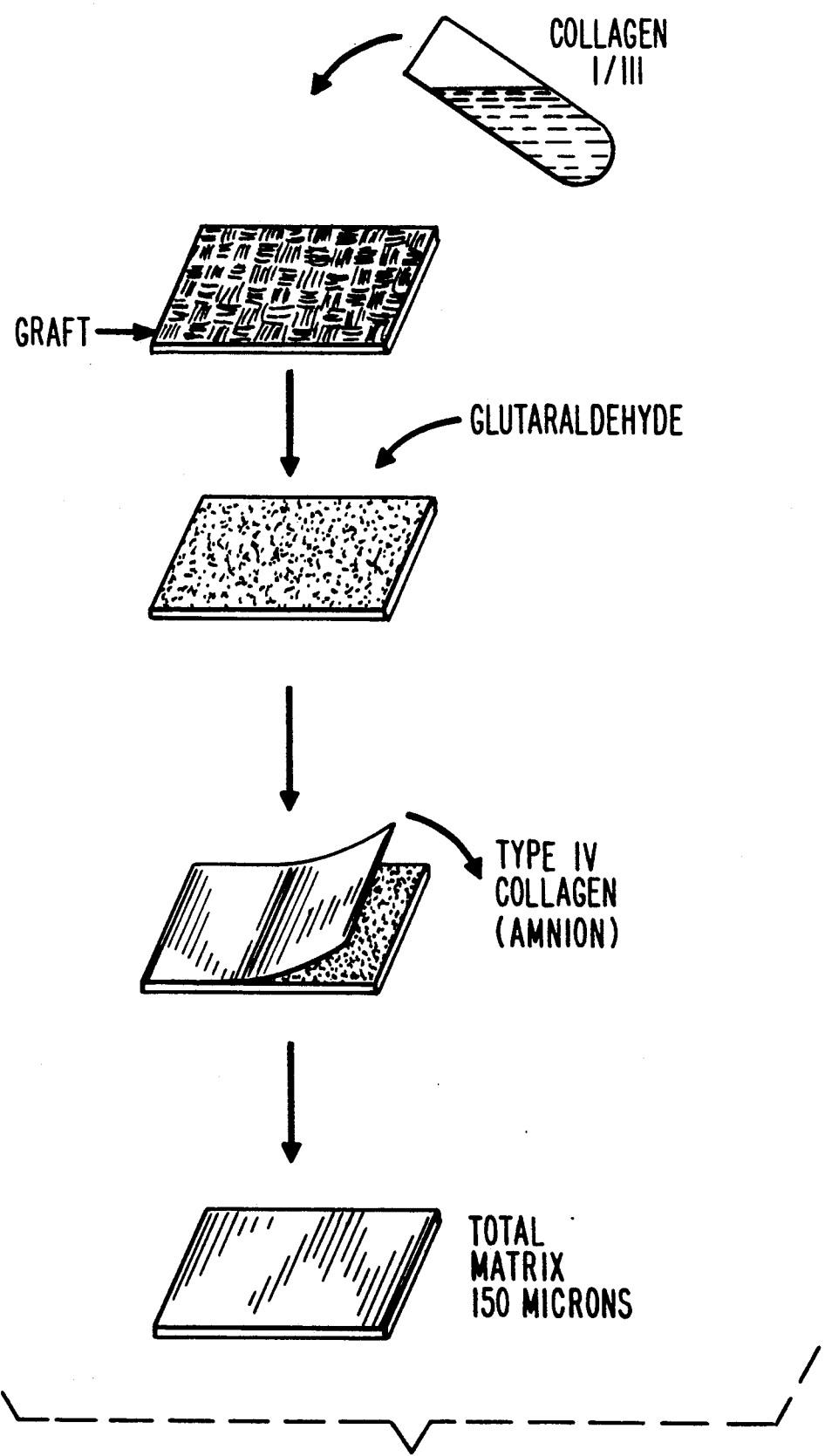
FIG. 3 is a diagram illustrating the preferred method of preparing the graft of the present invention to have a collagen laminate with a Type IV/V collagen surface layer.

The preferred method of the present invention stems from work to investigate the function and characteristics of different types of endothelial cells. The method described herein permits the isolation of large quantities of microvascular endothelial cells from human microvascularized tissue (perinephric fat, omentum, or subcutaneous fat) under sterile conditions (e.g., the operating room). Procurement of large quantities of cells does not require tissue culturing subsequent to their isolation. These procedures are related to those developed during investigations concerning the isolation of non-human (rat) microvessel endothelial cells using rat epididymal fat as a source of tissue. The methods for isolation of non-human rat fat microvessel endothelial cells have recently been reported as being useful for the isolation and culture of human microvascular endothelial cells from skin and fat. Kern et al report that these isolated endothelial cells may subsequently be cultured and used in functional studies. *J. Clin. Invest.* 71:1822–1829 (1983). See also Jarrell et al, "Human Adult Endothelial Cell Growth In Culture", *Journal of Vascular Surgery* 1(6):757–764 (November, 1984) which is hereby incorporated by reference.

The present invention provides a novel method of using isolated microvascular endothelial cells for producing an endothelial cell lining on intravascular implants. Such implants include but are not limited to, for example, intravascular devices such as artificial vascular prostheses, artificial hearts, and heart valves. It is anticipated that the herein described procedures may lead to the development of other artificial organs or devices. These organs and devices will receive circulating blood either following implantation or in an extracorporeal circuit, and the present procedures provide a non-thrombogenic or anti-thrombogenic interface between the blood and the implanted surface. The immediate objective of the present invention is the use of the herein disclosed methods for endothelializing surfaces composed of known synthetic materials, such as polyester and polytetrafluoroethylene, or naturally occurring materials, such as an umbilical vein, saphenous vein, and native bovine artery.

The present invention provides a method of treating an implant intended for implantation in a human patient comprising: obtaining human microvascular rich tissue from that patient; separating microvascular endothelial cells from that tissue; and placing said microvascular endothelial cells onto said implant to provide at least about fifty percent (50%) confluence of said cells on the surface of said implant to be treated. This method is quick and relatively simple, and facilitates the implantation of a prosthesis or surface which has been treated with the patient's own "fresh" (uncultured) endothelial cells. Since the surgical procedure may be performed in its entirety in a single sterile environment, the likelihood of contaminating the endothelialized graft is minimized.

The method of the present invention provides for the isolation of large quantities of endothelial cells without the need for tissue culturing. Yet, the procedures involved may be readily performed in an operating room. A general flow diagram of the procedure for separating microvascular endothelial cells from a patient's tissue is illustrated in FIG. 1. While these procedures may also be used for the isolation of endothelial cells from tissues other than fat, such as brain, lung, retina, adrenal glands, liver and muscle, the use of fat tissue as the source for the cells is preferred due to its abundance and availability, and due to the fact that its removal should not adversely affect the patient being treated. Accordingly, as shown in FIG. 1, an amount of human microvascularized fat (A) may be procured from a number of sources. Although less preferred, it is possible to obtain human perinephric fat from brain-dead but heart-beating cadaver donors, or from donors other than the patient during the donor's surgery. In any event, the donated tissue is then immediately transferred to ice cold buffered saline (pH 7.4) wherein the buffering agent is preferably a phosphate, i.e., a phosphate buffered saline (PBS). The tissue is minced (Step B) with fine scissors and the buffer decanted. The proteolytic enzyme collagenase, containing caseanase and trypsin, is added to the tissue and incubated at 37° C. until the tissue mass disperses. This digestion occurs within thirty (30) minutes, and generally should be less than twenty (20) minutes. The digest is transferred to a sterile test tube and centrifuged (Step C) at low speed (700 x g) in a table top centrifuge for five (5) minutes at room temperature. The pellet of cells thus formed consists of greater than ninety-five percent (95%) endothelial cells. These endothelial cells are described herein as microvascular endothelial cells (MEC) since they originate from the arterioles, capillaries and venules, all elements of the microvasculature. This MEC pellet is washed one time by centrifugation with buffered saline, preferably PBS, and can be used directly without further purification in the treatment (application) step described herein.

Alternatively, these microvascular endothelial cells may be further purified by centrifuging the cells with a continuous gradient (Step D of FIG. 1). This gradient can be formed from a number of large molecular weight solutes, including albumin, dextran, or commercially available density gradient materials, such as Percoll (Pharmacia Inc., Piscataway, N.J.) or Nycodenz (Nyegaard and Company, Norway). Gradient centrifugation is used to remove red cells, white cells and smooth muscle cells. A forty-five percent (45%) solution of Percoll has routinely been used in the studies reported herein. Cells are layered on the surface of the Percoll solution and centrifuged at 13,000×g for twenty (20) minutes. Alternatively, cells are layered on a performed Percoll gradient, and centrifuged at 400 x g for five minutes at room temperature. A thick band of endothelial cells results at the upper end of the gradient. These cells are removed with a pipette and washed one time by centrifugation with phosphate-buffered saline.

The microvascular endothelial cells derived from human microvascularized tissue may then be used directly in the seeding step of the present invention without further treatment or culturing for the application to vascular prosthetic surfaces. A major advantage of this procedure is the procurement of large quantities of endothelial cells from human tissue for the coating of vascular grafts. In addition, these cells can be obtained from the donor who will receive the prosthetic implant. This methodology thus permits treatment of implantable surfaces with autologous endothelial cells.

In accordance with one alternate method of the present invention, the prosthetic surfaces to receive the MEC can be used directly, without any pretreatment, in the condition in which they are packaged by the manufacturers. It may, however, be advantageous to at least pre-wet those surfaces with an aqueous solution. Preferably, the prosthetic surface should be pretreated. Pretreatment is used to accelerate the adherence, spreading and growth of endothelial cells on the surface.

In performing one alternate embodiment treatment step of the present invention, isolated human microvascular endothelial cells are suspended in a buffered saline which contains plasma-derived protein from the patient. This protein solution is prepared by mixing six parts buffered solution with one part plasma to produce a solution which contains approximately one percent (1%) protein. The data set forth in Table 1 indicates that endothelial attachment is affected by protein concentration in the suspension. As the data in Table 1 illustrates, the optimum protein concentration is about one percent (1%), and indicates the need for protein during surface treatment. Albumin is the preferred source of the protein, but non-plasma sources of protein can be used.

TABLE I

Effects of Varying Albumin Concentrations On The Initial Adherence and Growth of HAEC.
PERCENTAGE OF CONFLUENCE+

| ALBUMIN CONCENTRATION | TIME 2 HOURS | 24 HOURS |
|---|---|---|
| 0% | 36.5% | 63.6%* |
| 0.1% | 32.5% | 61.2%* |
| 1.0% | 47.7% | 67.9%* |
| 4.5% | 11.5% | 61.7%* |

+(#EC/$10^5$ cells/cm$^2$)
*Significant Change

The microvascularized endothelial cell suspension is then preferably pelletized by centrifugation (200 x g) and the pellet resuspended with protein-containing buffer solution. This resuspension should be performed at a ratio of approximately 1:5 to 1:15 or about 1:10 volumes of packed microvascular endothelial cells to buffer solution. The cell suspension is added to tubular grafts and the ends clamped, or the cells are layered upon the surface to be treated. Optimum periods for cell interaction have not yet been defined with precision, and vary depending upon the material of the prostheses, the nature of any pretreatments it may have received and whether the surface of the prostheses has been modified to improve its acceptance of the microvascular endothelial cells. For example, it has been found that the adherence of endothelial cells requires two hours on an untreated polyester graft surface, and less than ten minutes on similar surfaces pretreated with protein. This adhesion behavior has been confirmed by scanning electron micrographs of human microvessel endothelial cells (MEC) on plain, untreated Dacron grafts. Following incubation for a sufficient time to permit adherence of the endothelial cells with the graft surface, the surface is washed with a protein containing buffer. The prosthesis can now be implanted in its normal manner.

It has been found, based on both biochemical data and morphological data, that human microvascular endothelial cells will adhere to untreated graft surfaces. Scanning electron micrographs show that human MEC placed onto untreated Dacron polyester using procedures described above will result in adherence, followed by cell coverage (complete confluence) following one day in culture. The cells attach to specific areas on the graft and do not exhibit complete coverage of untreated graft surfaces. When human MEC are seeded onto plasma-treated Dacron polyester grafts, the coverage is much greater initially as compared to untreated Dacron surfaces. Scanning electron micrographs illustrate near confluent coverage of plasma coated grafts with human MEC. Table 2 illustrates the adherence and growth of human microvessel endothelial cells on untreated and protein-coated Dacron polyester grafts, initially at day 1, and after fourteen (14) days.

TABLE 2

Adherence and growth of human microvessel endothelial cells On untreated and protein coated Dacron grafts.
PERCENTAGE OF CONFLUENCE+

| DACRON PRETREATMENT | EC-0 | | EC-2 | | EC-10 | |
|---|---|---|---|---|---|---|
| TIME (DAYS) | 1 | 14 | 1 | 14 | 1 | 14 |
| UNTREATED | 37% | 37% | 43% | 56%* | 44% | 38% |
| COLLAGEN (Type I/III) | 29% | 31% | 59% | 68% | 47% | 26% |
| COLLAGEN (Type I/III) AND PLASMA | 34% | 44% | 47% | 76%* | 66% | 39%* |
| PLASMA | 53% | 55% | 65% | 100%* | 63% | 35%* |

+(# EC/$10^5$ cells/cm$^2$)
*SIGNIFICANT CHANGE

As Table 2 indicates, MEC adherence is facilitated by protein treatment of graft surfaces. It has also been found that the endothelial cell proliferation on prosthetic surfaces is stimulated by the presence of protein treatment.

As described above, the establishment of an intact monolayer on a prosthetic surface might be most beneficial if created prior to implantation. This endothelialized surface, if shear resistant, would provide an immediate anti-thrombogenic surface. Accordingly, the shear resistance of microvessel endothelial cell layers has been investigated. Human fat was treated with collagenase for 25 minutes, washed and purified in a Percoll gradient separation. This yielded $1.25 \pm 0.45 \times 10^8$ cells per gram of fat. Following a 1 hour incubation on plasma-coated Dacron, $2.8 \pm 1.5 \times 10^4$ remained firmly adherent to the surface. When exposed to flow for 2 hours at a shear stress of 0 to 80 dynes/cm$^2$ between 50 to 100% of the initially adherent cells remained adherent. Statistical analysis of this data failed to demonstrate a strong relationship between the number of adherent cells and the shear rate. Scanning electron microscopy demonstrated endothelial cells in various stages of attachment to the plasma-coated Dacron. Although most cells were still round and only focally attached to the surface, some cells were maximally flattened, forming cell to cell contact. Because of high cell yield and the firm adherence characteristics, microvessel endothelial cells may offer the possibility for confluent endothelial cell seeding of a graft at the time of surgical implantation without the need for cell culture.

By way of further example, the adherence of endothelial cells to protein treated surfaces was tested under shear stress in order to simulate conditions which would exist when an endothelial cell seeded graft is subjected to arterial flow following implantation. Human adult microvascular endothelial cells were isolated from human peri-nephric or omental fat which was obtained from brain-dead, heart-beating cadaver organ donors or patients undergoing unrelated surgical procedures in accordance with IRB protocol. The fat was mechanically minced and placed in sterile 50 ml screw cap Erlenmeyer flasks containing 10 ml of Dulbecco's Cation Free (DCF) buffer, pH 7.4, with collagenase (Worthington Type I; Cooper, Biomedial, Malvern, Pa.) 4 mg/ml and bovine serum albumin (Sigma Type V; Sigma Chemical Co., St. Louis, MO) 4 mg/ml. The flasks were incubated for 25 minutes at 37° C. with gentle agitation. The contents of the flask were centrifuged at 200 x g for 7 minutes. The pellet was washed twice in DCF buffer containing 0.1% BSA and spun for 3 minutes at 200 x g.

The resultant pellet was resuspended in 45% Percoll (Pharmacia Fine Chemicals, Piscataway, N.J.) in DCF and centrifuged at 20,000 x g for 20 minutes at 4° C. The tufts of capillary endothelial cells were in a milky-white layer at the top of the density gradient with vessel fragments and cellular debris in the pellet. The capillary endothelial cells were washed twice in DCF-BSA buffer at 200 x g for 3 minutes. The tufts were resuspended in medium 199 with 20% fetal calf serum (Hazeltown Research Labs, Denver, Pa.). The identification of endothelial cells in the primary isolate is based primarily on morphological examination by phase contrast microscopy. Primary isolates, plated at high density and subjected to primary culture, exhibited positive staining for Factor VIII-related antigen, and displayed angiotensin-I-converting enzyme (ACE) activity.

The graft surface was prepared using the following procedure. Cooley Graft Woven Porosity Dacron Fabric (supplied by Meadox Medicals, Oakland, N.J.) was serially washed in acetone, 8.5% $H_3PO_4$, and 1 N NaOH; this was followed by extensive washing with double distilled $H_2O$. After drying, it was placed in a Harrick plasma cleaner (Harrick Industry, Ossining, N.Y.) for 10 minutes at $10^{-4}$ torr in an air atmosphere. A 2.5 × 5 cm segment of the graft material was prepared for substrate coating and endothelial cell seeding.

The Dacron graft material was then treated with platelet rich plasma. Platelet rich plasma (PRP) was prepared from freshly anticoagulated (ACD) whole blood from normal human donors. The PRP was mixed with 50 mM $CaCl_2$ just prior to graft treatment. The PRP was then placed onto the graft material immobilized in a seeding chamber. Once treated with PRP, a fibrin clot was permitted to form at 37° C. on the graft surface. The excess clot was then removed, and the graft surface was washed with culture medium prior to EC seeding.

The woven Dacron graft immobilized in the seeding chamber and coated with PRP was seeded with $5 \times 10^5$ EC in 0.5 cc of culture medium placed in the seeding well (1 cm$^2$ area) to allow incubation to occur over 1 hour in a 37° C. incubator. Following incubation, the supernatant was removed, and the graft surface was lightly washed with culture medium. Control chambers were filled with 0.5 cc of fresh culture medium and placed in an in vitro circulatory loop. The EC were then exposed to a single shear stress between 0 and 80 dynes /cm$^2$ for 2 hours at 37° C. using recirculated culture medium. During flow, negligible changes in pressure gradients, pH and electrolyte concentrations were observed. Shear stresses were calculated using the formula for momentum transport between parallel plates. See Bird et al, *Transport Phenomena*, New York, 1960, John Wiley & Sons, Inc. pp. 1–70. The maximum Reynolds number calculated for our study was 600, suggesting laminar flow. Furthermore, flow versus pressure measurements revealed a linear relationship throughout the shear rates encountered. At the termination of flow, the chambers were disassembled, and the graft surfaces were examined by light and scanning electron microscopy.

Light microscopy was conducted on seeded grafts which were washed with Dulbecco's phosphate buffered saline containing 0.1% BSA and then fixed with 95% ethanol for 15 minutes. The grafts were rinsed with distilled $H_2O$ and stained with Gill's Hematoxylin (Fisher Scientific Co., Fairlawn, N.J.). After two rinses with distilled $H_2$, the grafts were placed in Scott's Tap Water Substitute for 1 minute. The surfaces were rinsed twice with distilled water and 95% ethanol. The stained grafts were then examined with a Nikon Diaphot microscope.

Scanning electron microscopy was also conducted. Seeded graft surfaces were fixed with 1% glutaraldehyde for 1 hour and 3% glutaraldehyde for 2 hours. They were then washed three times for 20 minutes each with Tyrodes cacodylate buffer (pH 7.4). Samples were postfixed in 1% $OsO_4$ for 30 minutes and washed 3 times with Tyrodes buffer. The samples were critical point dried and sputter coated with gold palladium. Mounted samples were examined in a Phillips scanning electron microscope.

Indium labelling of endothelial cells was also conducted. Endothelial cells were isolated from the microvascular as described above. Cells were pelleted by centrifugation for 3 minutes at 100 x g, and washed once with PBS (pH 7.4). The cells were resuspended prior to labelling in 0.5 ml of PBS. The cell concentration was adjusted to $2.5 \times 10^5$ cells /ml. 20 microcuries of Indium (as Indium[111] oxine, Medi-Physics, Emeryville, Calif.) were added to the cell suspension, and the cells were permitted to label for up to 30 minutes were undergoing general agitation. Just prior to washing, a 5 ul sample was removed to permit final analysis of labelling efficiency. Labelled cells were washed 3 times by centrifugation using complete tissue culture medium. The final pellet was resuspended in complete culture medium to a final concentration of $2.5 \times 10^5$ cells/ml.

Adherence quantitation of radiolabelled EC was determined using the following procedure. The EC were seeded onto PRP coated Dacron immobilized in Beem capsules (Polysciences, Inc. Fort Washington, Pa.) and incubated for specific time intervals (t = 10, 20, 30, 60, 120 minutes). At each time interval, samples were examined. The culture medium was removed and PBS was forcefully pipetted across the surface. The entire Beem capsule was submitted for analysis. The mean at each time point was calculated and maximal adherence was plotted as percent versus time.

EC counts on the flow and control slides were made with a Micro-Comp Grain counter supported by an IBM PC AT and Frame Grabber. The data obtained during the flow analysis was evaluated in two ways. Firstly EC adherence is expressed as the percentage of cells that remained adhered after flow compared to the control slides. Each point represents at least 4 observations and in some as much as 8. This was plotted versus shear stress and linear regression analysis was performed on this curve to determine statistical significance. Secondly, comparisons of initial adherences were made using the Student's t-test.

EC adherence as determined by Indium[111] labelling was plotted against time. Each data point represents the mean of two separate samples.

In this test, adipose tissue was obtained from 13 individual donors and included perinephric and omental fat sources. EC were successfully isolated from all 13 donors. Elapsed time for the 3 stages of EC isolation were $29.9 \pm 3$ (mean ± standard error of the mean) minutes for collagenase, 20 minutes for Percoll and 30 minutes for washes and handling for cell counts. Mean EC yield per gram of wet fat was $1.25 \pm 0.45 \times 10^6$ cells. Cell viability as determined by Trypan Blue dye exclusion exceeded 95% for all isolations.

Figure 6:
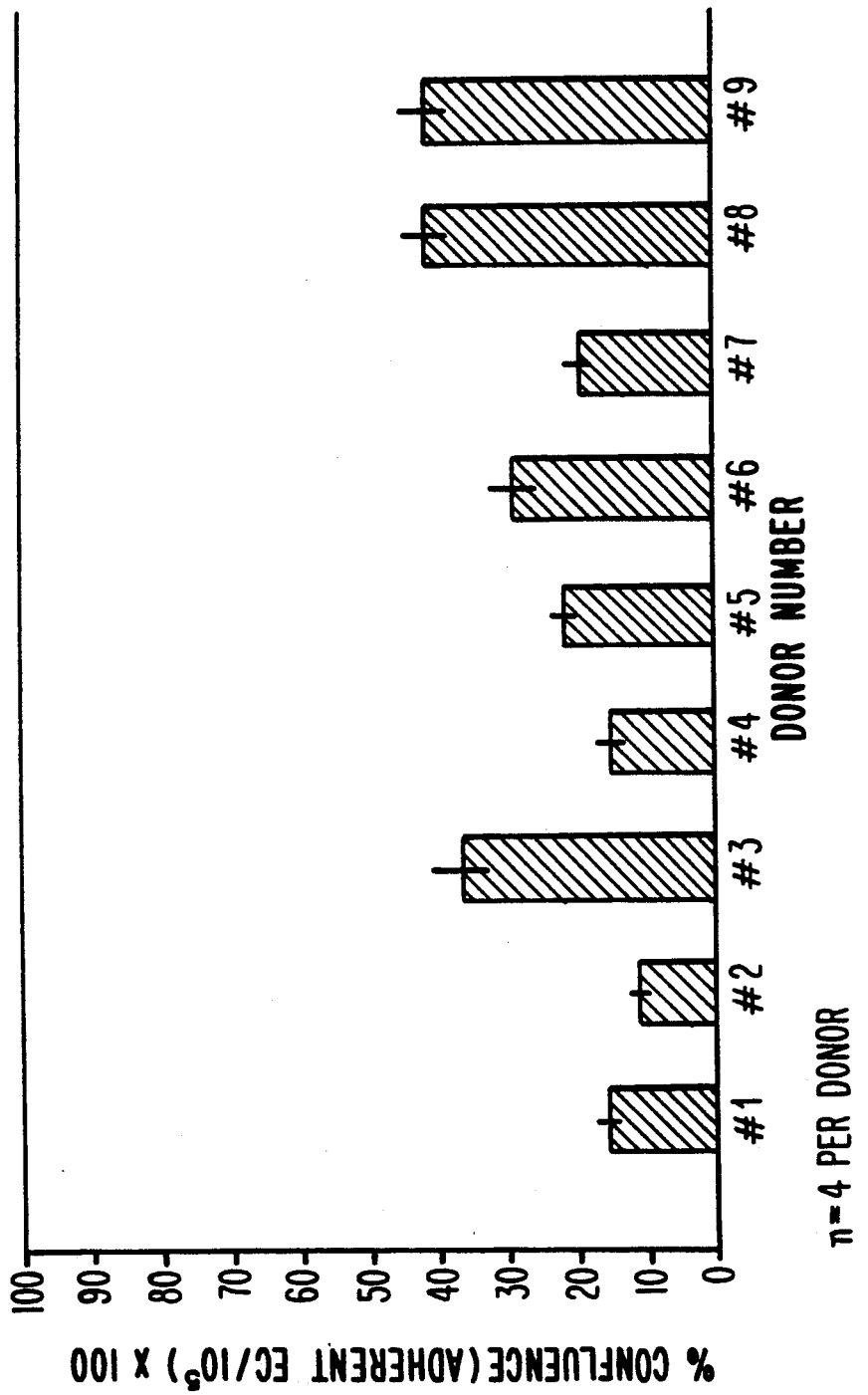
FIG. 6 is a bar graph of microvessel endothelial cell exhibited donor to donor differences in initial adherence to plasma coated Dacron. Freshly isolated microvessel endothelial cells were seeded onto plasma coated Dacron for 1 hour. After a brief wash, the grafts were stained with Gill's hematoxylin and adherent endothelial cells counted. Donors #8 and 9 demonstrated statistically significant increased adherence compared to #1, 2, 4, 5, 6, and 7 and #3 is different from #1, 2, 4, 5, and 7, as determined by a Student's t-test.

Following a 1 hour incubation on plasma coated Dacron, endothelial cell adherence as evaluated by light microscopy was $2.8 \pm 1.5 \times 10^4$ cells/cm$^2$ (n=9). Adherence was measured as percent of confluence. This was determined by counting the number of adherent endothelial cells following a 1 hour incubation and dividing it by $10^5$, which is the maximum number of EC present in a confluent monolayer regardless of the cell seeding density. Four separate adherence measurements were made per donor for statistical analysis. As seen in FIG. 6, the standard error of the mean for adhesion for each individual donor was small, in contrast, the mean adherence varied from $1.13 \times 10^4$ EC/cm for donor #2 to $4.11 \times 10^4$ EC/cm$^2$ for donor #9. Donors #8 and 9 demonstrated significantly higher initial adherence (p less than 0.05) compared to #1, 2, 4, 5, 6, and 7 and #3 was significantly different from #1, 2, 4, 5, and 7 by the Student's t-test.

Figure 7:
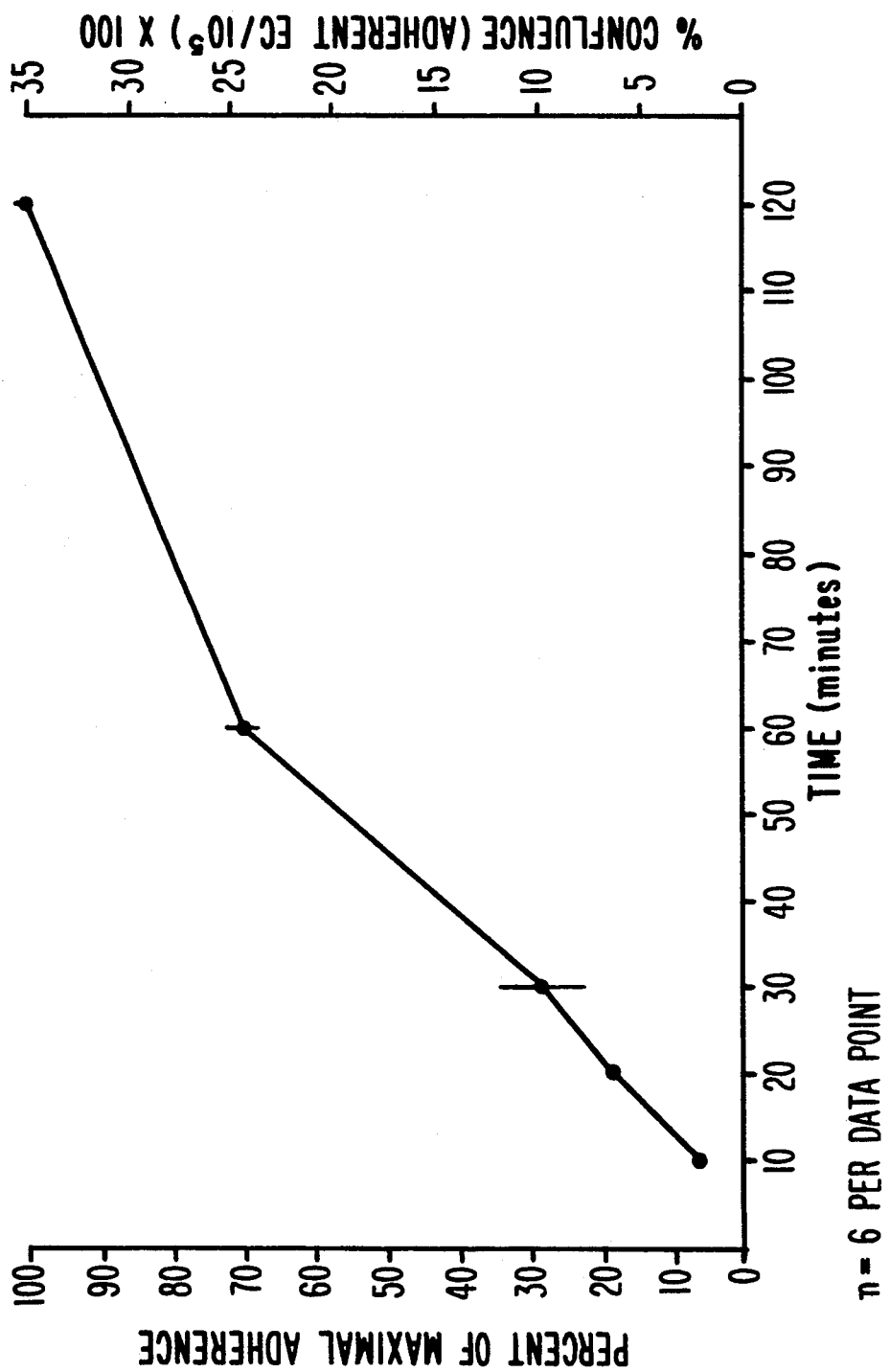
FIG. 7 is a chart of the temporal sequence of Indium$^{111}$ labelled microvessel EC adherence to plasma coated Dacron. EC were permitted to associate with a graft surface for the time shown, followed by the removal of non-adherent cells as described hereinafter. Radiolabelled cells exhibit a rapid rate of adherence for 60 minutes followed by a decreased rate until the final 120 minute adherence evaluation. Data represents the mean of 6 samples±standard deviation.

The temporal sequence of microvessel endothelial cell adherence to plasma treated Dacron was also investigated in this test. Microvessel endothelial cell radiolabelled with Indium$^{111}$ were plated onto plasma treated Dacron and cell adhesion analyzed over a 120 minute period (see FIG. 7). The left y-axis represents the number of EC adherent at a given time point divided by the number of adherent EC after a two hour incubation (maximal adherence) expressed as a percentage. The right y-axis represents the number of EC adherent at a given time point divided by the number of initially seeded EC ($10^5$ EC/cm ) expressed as a percentage of confluence. A biphasic rate of adherence was observed, with an initial rapid rate of adherence during the first 60 minutes followed by a slower rate until the final time point of 120 minutes. Significantly, although limited, adherence was observed at 10 minutes, the earliest time evaluated.

Adherence to plasma coated Dacron with flow was further determined. Following a 1 hour incubation, the EC seeded surfaces were placed in the flow chamber and exposed to defined shear conditions. EC from each individual donor were exposed to only one shear rate. FIG. 8 demonstrates the effect of shear stress on adherence of EC to the Dacron. Data is expressed as a percentage of adherence to the Dacron graft. This was determined by counting the number of EC adherent to the surface following the 2 hour experiment and by dividing it by the number of EC adherent to the surface prior to incubation expressed as a percentage. EC from 13 donors were used. At each shear stress, 4 separate observations were made for a given donor. When EC from 2 donors were separately examined at a given shear stress (e.g.), 20, 30 or 50 dynes/cm$^2$), no significant differences in cell adhesion was observed. Linear regression analysis revealed a y-intercept of 91 and a slope of $-0.33$ with an r-value of -0.26. This statistical analysis supports the conclusion that the adherence of freshly isolated microvessel EC is not affected by shear stresses up to 80 dynes/cm2.

The qualitative evaluation of EC adherence was conducted by scanning electron microscopy. When cells were permitted to associate with the surface for 1 hour followed by shear for 2 hours, low power observations revealed areas with variable densities of EC. The Dacron surface was uniformly covered by the plasma clot and cells were observed to adhere to areas of plasma clot which overly both the peaks (warp) and valleys (weft) created during the weaving process. Higher magnification of areas considered by low power observation to display more limited cell association revealed the presence of EC in various stages of surface association. Cell morphology varied from flattened cells which exhibited a dramatic increase in cell surface area to cells which remained round with only focal attachment. All of the cells were resistant to shear.

This test thus supports the proposition that it is possible to generate an endothelium upon a prosthetic surface to avoid complications stemming from the thrombogenicity of prior art prosthetic surfaces. This test further demonstrates the feasibility of providing a prosthetic graft that is completely endothelialized at the time of implantation without precedent EC culture. This approach avoids the problem that only limited number of large vessels are available as EC donors whereas microvessels are universally present in high density in almost all tissues. These EC are relatively easily isolated from adipose tissue, yielding a high number of EC per gram of tissue in contrast to large vessels. In tissue culture these EC demonstrate many of the functional and morphological characteristics of large vessel EC. Most importantly they are able to form a contact-inhibited confluent monolayer that is quite similar to the cobblestone appearance of normal large vessel endothelium. Microvessel endothelial cells fulfill many of the requirements of a cell capable of rapidly endothelializing a graft. The cells are universally present in tissue, being present in adipose tissue, a donor tissue that can be removed in large quantities without significant surgical effort and with minimal risk to the patient. Such cells are easily and reliably isolated from most patients in 60 to 90 minutes, capable of producing large quantities of endothelial cells that are free of contaminating smooth muscle cells, quickly able to become firmly adherent to Dacron pretreated with PRP or other materials, such as basement membrane. They are further able to establish areas of confluent cells, able to withstand physiological shear stresses after only 1 or 2 hours of incubation, and are autologous to the donor.

The above described test demonstrates that adipose removed from diverse human donors yields $1.25 \pm 0.45 \times 10^6$ EC per gram of fat and that the initial adherence of these EC ranges from 10% to 40% of the applied EC even on grafts treated with PRP. Although a clear trend has not been identified regarding patient age, disease or social behavior, there is evidence that EC yield and adherence characteristics may vary among individuals. In spite of these differences, these adherence variables may be compensated for by increasing the amount of fat harvested.

The described test has also examined another important requirement, that the freshly isolated and seeded EC are able to withstand physiological shear stresses. The resistance of endothelialized surfaces to shear in a system that is similar to most in vivo seeding experiments has been conducted. In previous studies we have shown that EC can firmly adhere to a surface even if they do not readily form a confluent monolayer. Thus this model actually measures adherence of single cells to a surface and probably represents less than the ideal environment for cells when exposed to flow. Yet the EC adherence remained greater than 50%, and in most cases much higher than that at all shear stress levels encountered. This implies that once cell to surface interaction and attachment has taken place, the EC are very firmly adherent. There are many variables in this model, including donor variables, plasma variables, and incubation conditions that may be studied to more completely understand as well as optimize this process.

Another important property is that freshly isolated and seeded EC be able to rapidly form complete cell to cell interactions. Undoubtedly these interactions additionally protect the EC from shear stresses to help prevent the cells from being pulled off the surface. While cell to cell associations do occur on plasma coated Dacron to a limited degree, in the tests described hereafter more optimal surfaces are provided to promote such cell to cell interactions.

The above described experiment confirms that microvessel EC possess qualities that make them potentially excellent for graft endothelialization. The variables involved in the isolation procedures as well as subsequent surface adherence and cell to cell interaction are discussed more fully hereinafter. It should be noted, however, that the procedures discussed herein, and hereafter, are all compatible with the manipulation of autologous human tissue in an operating room environment.

The creation of the preferred confluent layer of endothelial cells on prosthetic surfaces is now believed to be dependent on at least three major variables. First, the initial adherence of cells should be sufficient to provide at least about fifty percent (50%) initial surface coverage. Procurement of large vessel endothelial cells to provide at least about fifty percent (50%) coverage is extremely difficult, if not impossible, since the only available source of cells is the patient's own large vessels. Although large vessel cells can be isolated and cultured to provide a large number of cells, the obvious problems associated with tissue culture media would then be presented. Microvascularized fat provides a rich source of endothelial cells for seeding. Twenty grams of the patient's fat will provide ample endothelial cells to seed a surface area of one hundred and eighty square centimeters (180 cm$^2$), the surface area represented by a typical femoral artery to popliteal artery bypass graft.

A second variable to be considered is the ability of endothelial cells to proliferate (grow) on a prosthetic surface. Application at fifty percent (50%) confluence requires the cells to duplicate one time to create a confluent cell layer. Table 2 shows that on the preferred protein coated surface (coated with platelet rich plasma), the cells will duplicate at least once in tissue culture media which contains growth factor. In the body, however, these growth factors would presumably not be present, and therefore, the ability to treat surfaces at or in excess of confluence is advantageous. Again, the availability of human MEC in large quantities permits the application of endothelial cells on a surface at densities capable of establishing a confluent monolayer or near confluent monolayer at the time of implantation.

These two variables are adequately addressed by applying human endothelial cells on prosthetic surfaces pretreated with proteins, as mentioned above, or upon surfaces which have been modified to emulate protein surfaces. Such modified surfaces are well-known to the endothelial cell tissue culture art. Alternatively, the endothelial cells may be "preclotted" into a fibrin (protein) gel which forms within and around the graft. Data indicate that human microvascular endothelial cells can be gelled within a protein meshwork, and following incubation in culture media, will migrate to the surface of the gel. This has been confirmed from scanning electron micrographs which show human microvascular endothelial cells forming a confluent monolayer on the surface of a Dacron polyester graft after these cells were preclotted in human plasma.

A third important variable is the effect which the technique and underlying surface have upon the functional characteristics of EC monolayer, including its morphology, resistance to shear, and antithrombogenic characteristics. To improve such functional characteristics, the interaction of human adult endothelial cells (HAEC) with the natural collagen surfaces presented by human amnion has been investigated. Scanning electron microscopic evaluation reveals that HAEC adhere rapidly to both the basement surface (collagen IV/V) and interstitial surface (collagen I/III) of amnion. However, the adherence of cells is significantly greater on the basement membrane surface. In addition, HAEC rapidly form close cell-cell interactions on basement membrane as compared to cells seeded on to the interstitial surface. These results suggest that seeding of endothelial cells onto artificial surfaces will be facilitated if the surface simulates the natural basement membrane to which endothelium natively adhere.

As mentioned above, recent evidence suggests that endothelial cells will adhere to and form at least loose cell-cell interactions with untreated graft and/or collagen-coated prosthetic surfaces. Such evidence, however, fails to show that such endothelial cells will form tight cell-cell complexes such as exist in native human vessels. However, the initial interaction of human endothelial cells with the native substrate to which endothelial cells normally adhere is quite important. In particular, the use of isolated human amnion is proposed since amnionic membrane, when denuded of epithelial cells, is of the same chemical structure as the surface underlying endothelial cells in normal human vessels. Both the prepared amnion and native vessels, excluding their endothelial cell surface are composed of basement membrane of both Types IV/V collagen with an underlying Type I and III collagen matrix.

To demonstrate the feasibility of the subject surface, human adult endothelial cells were isolated and cultured according to the procedures published by Jarrell et al, "Human Adult Endothelial Cell Growth in Culture", J. Vasc. Surg. 1(6):757-64 (1984), and as described in the above-identified related patent application. These cells were seeded onto the prepared amnion, thus providing a system by which initial adherence of endothelial cells to a substrate simulating that of native human vessels could be studied. The evaluation was done utilizing light and scanning electron microscopy.

Human amnionic membrane, taken from fresh human placentae, were prepared by a modification of the method described by Liotta et al. "New Method For Preparing Large Surfaces of Intact Human Basement Membrane For Tumor Invasion Studies", Cancer Letter, 11:141-152 (1980). All procedures were under sterile conditions. The inner amnionic membrane was gently bluntly dissected away from the chorion, and was then washed twice in ice-cold phosphate-buffered saline with 100 units per milliliter penicillin and 0.25 mcg/ml Fungizone. Following this the membrane was washed once in Dulbecco's minimal essential media at 4° C., rinsed once with distilled water with one mM N-ethylmaleimide for 1 hour at 4° C. The amnion was then incubated for 2 hours at 20° C. in 4% deoxycholate solution, thus loosening the epithelial cells without damaging the structure of the underlying basement membrane. Gentle agitation with a rubber policeman denuded the epithelial cells from the basement membrane. The integrity of the basement membrane was then verified using India ink staining. The removal of the epithelial cells was verified morphologically.

The amnionic membrane, prepared and deepithialized as described above, was then immobilized in plastic capsules similar to those used by Williams et al in "Adult Human Endothelial Cell Compatibility with Prosthetic Graft Material", *J.Surg. Res.*, supra. This provided a stable, well-defined surface area of amnion (0.5$^2$ cm) for subsequent seeding with and proliferation of endothelial cells (EC). Both basement membrane and interstitial collagen sides of the amnion were prepared for cell seeding. Prior to tissue cultural studies, the capsules with amnion were soaked overnight at 4° C. in complete media with 50 mcg/ml penicillin/streptomycin and 0.25 mcg/ml fungizone.

Human adult endothelial cells were isolated from vascular tissue procured from brain-dead, heart-beating cadaver renal donors and were cultured according to the published procedures referenced above. In this study, EC from adult human iliac vein were used. Briefly cells were isolated from a fresh iliac vein by treating the luminal surface with collagenase (Worthington Type I, Worthington Diagnostic Systems, Inc., Freehold, N.J.) and grown in 25 cm$^2$ tissue culture flasks precoated with gelatin (1%) in culture medium (medium 199, 20% heat-inactivated fetal calf serum, 90 ug/ml heparin (procine), and 20 ug/ml endothelial cell growth factor. Cells used for amnion seeding experiments were calculated to have cumulative population doublings of between 16 and 25. Population doublings were calculated by the formula PD=log$_2$ (number of cells harvested)/(number of cells seeded×attachment efficiency) and summed to give the cumulative population doubling (CPDs). The EC identity of these cells has been previously reported and included positive staining for factor VIII related antigen, cobblestone morphology and the expression of EC specific prostaglandin and angiotensin-converting enzyme activity.

Endothelial cell-seeded amnion was fixed with 2% glutaraldehyde overnight, then formation fixed, paraffin embedded, and sectioned for subsequent hematoxylin and eosin staining. The stained sections were then examined under brightfield illumination in a Nikon diaphot microscope.

For scanning electron microscopy, the EC-seeded amnion was fixed with 1% glutaraldehyde for 1 hour, 2% glutaraldehyde for 2 hours, and then washed four times (20 minutes each) in Tyrodes cacodylate buffer pH =7.4. The amnion was then dehydrated in a gradel series of acetone, critical point dried, and coated with gold-palladium. At this point, the plastic capsules were removed from the seeded amnion samples. These were then mounted and examined in a Phillips scanning electron microscope.

Human amnionic membrane, prepared according to the methods described above, was able to withstand the denudation procedures involved. Maintenance of the basic basement membrane structure was established by scanning with India ink. Integrity of the membrane was also evidenced by the observation of intact amnion surfaces-i.e., surfaces devoid of damage, rips or tears, when samples were examined using light and scanning electron microscopy. In addition, the efficacy of the deepithelialization procedure was demonstrated when unseeded, denuded, control amnion remained free of EC.

Human iliac vein endothelial cells (HIVE) were isolated and grown in tissue culture as an established cell line. Cells were seeded at confluent densities onto either the basement membrane or the stromal collagen component of the amnion. Samples of cells seeded onto either side were incubated for two hours prior to washing and fixation, and subsequently examined to evaluate initial adherence of the EC with substrate. Observation with scanning electron microscopy showed substantial initial adherence of both Types IV/V (basement membrane) collagen and Type I/III (interstitial) collagen. A layer of confluent EC was achieved and maintained on the IV/V collagen, and it was observed that many of the cells exhibited tight cell-cell association, while some cells were observed to loosely associate with the surface. On the I/III collagen matrix cells adhered but at a lower density and with looser cell association than seen on IV/V collagen. Following 7 days in tissue culture, light microscopic evaluation revealed the adherence and spreading of cells to both I/III and IV/V collagen surfaces.

The subject experiment thus demonstrated that human amnionic membrane, obtained from fresh human placentae, can be prepared to yield a large surface of native human basement membrane. This design provides a plentiful, readily available source of substrate which simulates the surface which the EC would experience in native human vessels. Thus, it is an ideal in vitro model with which to study the initial and prolonged interaction between seeded HAEC and collagen surface such as exist in vivo. Using amnion, the HAEC have been demonstrated to adhere well to both basement membrane and interstitial collagen matrix during the first two hours of association, however cells on basement membrane formed tight cell-cell interactions which resemble the association of endothelial cells in native vessels. This suggests that substances which simulate native human basement membrane would enhance EC-graft interactions, and result in a decreased incidence of graft occlusion. These results have been reported in Baker et al, "Endothelialization of Human Collagen Surfaces with Human Adult Endothelial Cells", of which the applicants are two coauthors, appearing in the *American Journal of Surgery*, 150:197-200 (August, 1985). The subject of that paper was orally presented at the 13th Annual Meeting of th Society for Clinical Vascular Surgeons, Rancho Mirage, Calif., Apr. 10-14, 1985. This paper, and particularly the figures (photographs) which cannot be conveniently reproduced in this application, are hereby incorporated by reference.

Further studies focused upon the temporal sequence of events from the initial contact of the endothelial cells to a surface through the establishment of a monolayer. Cultured human adult EC were radio-labelled, seeded onto Dacron, and adherence was quantified after vigrous washing. Firm adherence of 70% of the seeded EC was seen by two hours to untreated Dacron, by 30 minutes to Dacron pretreated with a collagen laminate in accordance with the present invention (interstitial Type I/III) collagen underlayer and amnion-derived basement membrane (Type IV/V) collagen surface layer, and by 10 minutes to plasma coated Dacron.

Parallel samples were morphologically examined by scanning electron microscopy to evaluate the adherence of endothelial cells to surfaces. Endothelial cells seeded on plain Dacron exhibited limited adherence, while cells on plasma treated Dacron exhibited limited cell to cell associations. On basement membrane treated Dacron, by 30 minutes the endothelial cells exhibited a flat attenuated morphology, completely covering the graft surface. This time frame is compatible with most vascular procedures, making an immediately endothelialized graft feasible.

The temporal sequence of events to establish confluence using autologous seeding is of particular importance in improving the short-term patency of small caliber grafts. In most animals other than humans, it is predicted that a period of 4–6 weeks following implantation would be required for a significant percentage of the graft to be spontaneously endothelialized. If this time frame is compared with most human lower extremity prosthetic graft clinical series, it is noted that a large percentage of graft failures due to thrombosis occurs within the first month following implantation. Thus establishment of an intact endothelium upon a graft at or near the time of implantation might be necessary, or would at least be desirable, before a significant effect on short term patency could be seen.

In order to achieve superior small caliber grafts, one requires a ready source of large quantities of autologous endothelial cells, such as those derived from microvascular fat. The prosthetic surface substrate should be selected to be receptive to endothelial cells, and the procedure should be conducted with knowledge of the attachment requirements and temporal parameters necessary to allow both a functional as well as a shear resistance monolayer to reliably form. Accordingly, the following tests have been conducted to demonstrate that the temporal sequence of events from endothelial cell seeding upon a prosthetic surface to generation of a confluent monolayer is such that attainment of confluence is sufficiently swift to permit pre-endothelialization at the time of implantation.

In conducting the following studies, endothelial cells were isolated from vascular tissue procured from brain-dead, heart-beating cadaver renal donors, and were cultured using the procedures described above. In this study, endothelial cells from adult human iliac vein, isolated as described above, were used. Preparation of human basement membrane was conducted, also in accordance with the above-described procedure. Heterologous interstitial collagen Types I/III were prepared from human placentae following the procedures of Madri, "The Preparation for Type V Collagen" In: H. Furthmayr, ed. The immunochemistry of extracellular matrix, Boca Raton, Fla.: CRC Press, 1982 (1):75–90, which paper is hereby incorporated by reference. Briefly, minced and freeze-dried placentae was pepsin digested and a collagen fraction was solubilized with 0.5 M acetic acid. Types I/III were precipitated with 1.4 M Na Cl and the precipitate was collected and dialyzed extensively against buffer. The white flocculant collagen was either used immediately or freeze-dried and stored at −20° C. until use.

In accordance with the preferred embodiment of the present invention, the surface of the graft was prepared as follows. The surface of woven Dacron graft was coated with heterologous interstitial collagens Types I and III prepared as described above. Following the stabilization of that collagen in 0.0174 M acetic acid and dilution to 0.32% collagen with ice-cold medium 199 and $NaHCO_3$. Deposition was promoted by allowing grafts to sit overnight at 20° C. The surface was then covered with 0.2% glutaraldehyde for 1 minute and rinsed with plain medium. Prepared amnion was then overlayed onto the graft surface with the basement membrane surface oriented away from the Dacron surface. This was incubated at 37° C. for 2 hours to promote graft to amnion adhesion. The amnion coated graft was then immobilized within a plastic ring (Beem capsule, polysciences F.W.) providing a 0.5 $cm^2$ surface area. In this respect, the subject technique is that described in Williams et al, "Human Adult Endothelial Cell Compatibility with Prosthetic Graft Material", J. Surg. Res., 38:618–629 (1985), which paper is hereby incorporated by reference.

For purposes of comparison, other Dacron graft surfaces were treated with platelet rich plasma. Platelet rich plasma (PRP) was prepared from anti-coagulation (acid-citrate dextrose) whole blood from human donors. PRP was mixed with 50 mM $CaCl_2$ just prior to graft treatment. Grafts were treated with PRP and a fibrin clot was permitted to form at 37° C. The clot was washed with cultured media prior to EC seeding.

The following procedure was used to examine the endothelial cell seeded grafts using scanning electron microscopy. EC derived from iliac veins were grown to confluence in 25 $cm^2$ flasks and used for cell seeding after two cell passages at a 1:4 split ratio. EC were briefly (1.5 minutes) washed with trypsin solution (0.25% trypsin with 0.09% EDTA in normal saline), washed once with culture media, and resuspended in complete culture media prior to graft surface seeding. EC were seeded at a cell concentration sufficient to provide a 100% confluent monolayer of cells on gelatin coated plastic surfaces. This density is equal to $1 \times 10^5$ cells/$cm^2$.

At appropriate times seeded graft surfaces were washed free of non- or loosely adherent cells by forcing complete culture media through a Pasteur pipette directed over the seeded graft surface. Graft surfaces were immediately fixed in 1% glutaraldehyde and prepared for scanning electron microscopy.

The scanning electron microscopy was performed after fixing with 1% glutaraldehyde for 1 hour, 2% glutaraldehyde for 2 hours, 3 washings (20 minute period) with tyrodes cacodylate buffer (pH 7.4) and dehydrated in a graded series of acetone. The grafts, still immobilized within plastic rings, were then critical point dried and coated with gold palladium. Mounted samples were examined in a Phillips scanning electron microscope.

Endothelial cells were radiolabelled for this test using two separate procedures. Thymidine labelling was performed by treating confluent EC in a T-25 flask with a trypsin solution. These cells were then washed with culture medium, counted and replated onto a T-75 flask at $10^4$ EC/$cm^2$. After 24 hours of growth, 0.5 uCi of tritiated thymidine (Amersham, Arlington Heights, Ill.) was added to the flask and incubated for 24 hours. The radioactive supernatant was removed and incubated for 24 hours. The EC were treated with trypsin solution and counted on a scintillation counter. Indium$^{111}$ labelling was performed on endothelial cells grown to confluence in 25 $cm^2$ flasks. The cells were briefly trypsinized. Released cells were pelleted by centrifugation (100 x g; 3 min) and washed once with phosphate buffered saline (pH 7.4). The cells were resuspended just prior to labelling in 0.5 ml of phosphate buffered saline. The cell concentration was adjusted to $2.5 \times 10^5$ cells/ml. Twenty microcuries of Indium[111] (Medi Physics, Emeryville, Calif.) were added to the cell suspension and cells were permitted to label for 30 minutes with gentle agitation. Just prior to washing a 5 ul sample was removed to permit final analysis of labelling efficiency. Labelled cells were washed 3 times by centrifugation using complete tissue culture medium. The final pellet was resuspended in complete tissue culture medium to a final concentration of $2.5 \times 10^5$ cells/ml.

The resulting radiolabelled endothelial cells were seeded and their adherence quantitated as follows. The endothelial cells were seeded on matrix coated Dacron immobilized in Beem capsules and incubated for specified time intervals (t=1, 5, 10, 20, 30, 60, 120 minutes). At each time interval, the following samples were obtained. The first sample, designated the "supernatant" was obtained by pipetting off the supernatant from the Beem capsule. The second sample, designated "loosely adhered", was obtained by vigorously washing the graft surface by forcefully pipetting culture medium three times onto the surface. The medium used to perform these washings was pooled and the entire specimen formed the second sample. The third sample, designate "adhered" was obtained by removing all adherent EC from the graft surface. This was performed by solubilizing EC samples in triplicate in 0.2 ml of 0.3% sodium dodecyl sulfate and transferring the resulting solution to filter paper. Each filter paper was transferred to 10% ice cold TCA and precipitated material was counted. The individual sample counts were normalized to percentages of the total number of counts in all three samples and plotted at % EC in each fraction versus time in minutes. EC labelled with tritiated thymidine were counted in a scintillation counter and EC labelled with Indium[111] were counted in a gamma counter.

Figure 4:
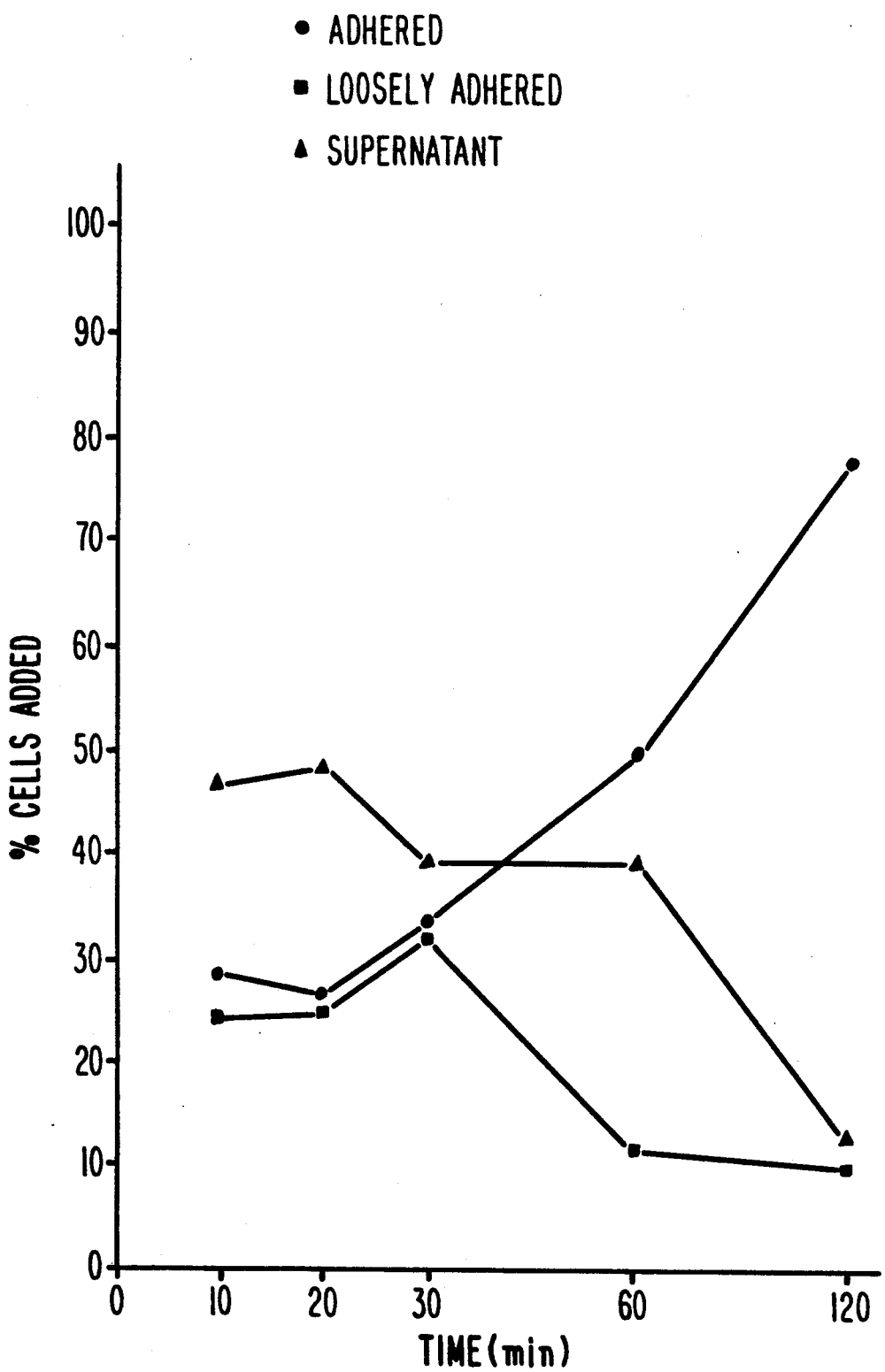
FIG. 4 is a graph showing the adherence of human adult endothelial cells to untreated Dacron grafts; endothelial cells were radiolabelled and cell association quantified as described herein. At designated times endothelial cells which remained free in the supernatant (triangles plot) were quantified. The graft's surface was then washed by expelling media from a Pasteur pipette over the surface and cells loosely adhered (square plot) and firmly adhered (circles plot) were quantified. Briefly cultured and minimally trypsinized endothelial cells exhibit a time dependent adherence to untreated Dacron.
Figure 5:
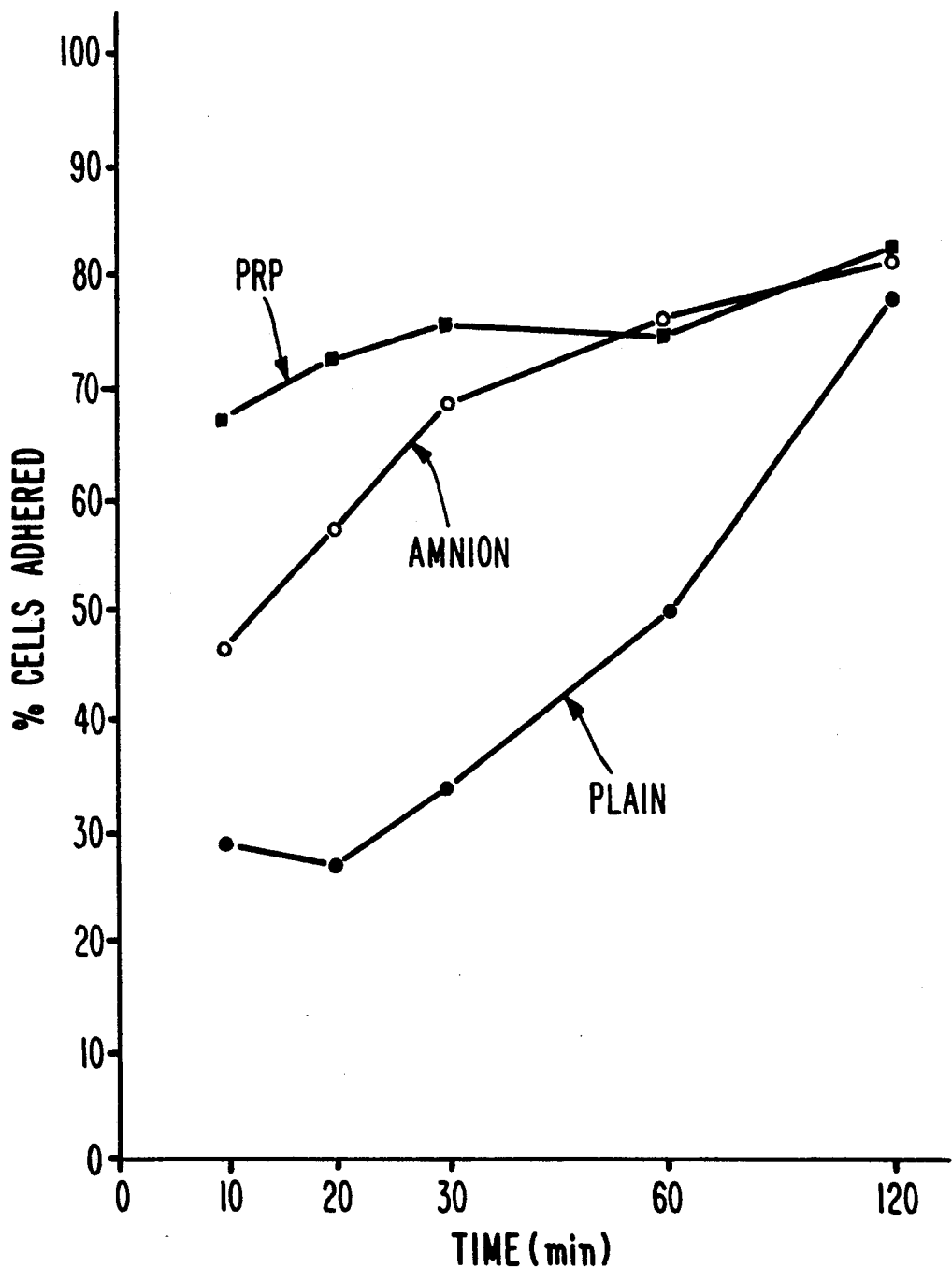
FIG. 5 is a graph comparing human adult endothelial cell adherence to untreated Dacron, and Dacron treated with either platelet rich plasma or human amnionic membrane. Establishment of a protein surface on Dacron accelerates the adherence of endothelial cells to the surface. The PRP plot refers to the surface resulting from clotting platelet rich plasma on Dacron. The AMNION plot identifies the surface resulting from the bonding of acellular amnionic membrane to the Dacron surface. The basement membrane surface of the amnion was oriented away from the Dacron surface. The PLAIN plot refers to untreated Dacron weave. Cellular adherence was quantified as described herein.

The following results were obtained from the above-described tests. The degree of endothelial cell adherence was quantitatively evaluated. The adherence of endothelial cells to graft surfaces were evaluated using both thymidine labelled and Indium[111] labelled cells. Both of these procedures provided similar results indicating that the method of cell radiolabelling does not affect the kinetics of cell adhesion. Human endothelial cells exhibited a time dependent adherence to untreated woven Dacron graft surface, as indicated in FIG. 4. By 10 minutes, approximately 30% of the added cells were observed to be firmly adhered to the Dacron surface. The number of firmly adhered cells gradually increased with time, with 50% firmly adhered by one hour and 80% of the added cells firmly adhered by two hours. Simultaneous quantitation of loosely adhered and non-adhered cells (FIG. 4) revealed that a major proportion of the cells which were not firmly adhered to the graft surface were free in suspension. By two hours of association with the graft surface cells which were either loosely adhered or free in suspension accounted for approximately 20% of the total cells added to the graft. When the graft surface was pretreated to produce a surface of either platelet rich plasma clot, or natural basement membrane surface prepared from human amnion, the rate of association of human endothelial cells was dramatically accelerated (FIG. 5). The PRP clot facilitated the rapid association of endothelial cells with 70% of the added cells firmly adhered following 10 minutes of incubation. The number of cells adhered to platelet rich plasma increased to a maximum of 80% by 2 hours. The initial adherence of human adult endothelial cells to human basement membrane (amnion) coated Dacron was intermediate between untreated Dacron and PRP treated Dacron (FIG. 5). The number of cells adhered increased with the time until the number of cells adhered to amnion equaled that adhered to PRP treated Dacron sometime between 30 and 60 minutes. As seen in FIG. 5, all of the surfaces exhibited approximately the same number of adherent cells following two hours of incubation.

The adherence of endothelial cells to the various graft surfaces was evaluated morphologically. The quantitative analysis of endothelial cell-graft interaction provided an analysis of the rate of endothelial cell adherence to the surface, but questions remained as to the form of interaction of endothelial cells with graft surfaces. We therefore evaluated morphologically the adherence of endothelial cells to basement membrane treated and platelet rich plasma treated graft surfaces, and to untreated Dacron itself. The temporal sequence of human adult endothelial cell adherence to basement membrane treated graft was determined by examining scanning electron micrographs. Following the addition of endothelial cells, graft surfaces were washed at several intervals between 1 and 120 minutes and evaluated by scanning electron microscopy. After just 1 minute, round endothelial cells were observed to be firmly adhered to the comparatively smooth amnion surface. Following 10 minutes of incubation, endothelial cells still maintained a round appearance suggesting focal adherence to a limited area of the cellular basal surface.

Evaluation of the endothelial cell adherence to basement membrane after 20 minutes of incubation provided the first evidence of cellular shape change. While spherical cells persist, cells with a more flattened morphology are observed. The edges of the more compressed cells are still rounded suggesting limited association of cells at their distal surfaces. An increase in the number of cells adherent after 20 minutes is also evident. At this time, numerous morphologies of endothelial cells adhering to the amnion surface are observed. Most easily identifiable are the presistance of round cells adhered to both partially and fully spread endothelial cells. The most numerous but least identifiable cell morphology is the extensively spread endothelial cells which provide a near complete cover to the original amnion surface. Endothelial cells which have not completely attenuated are also identifiable.

A complete morphological maturation of the endothelial cells seeded amnion surface is observed one hour after the onset of cell association. Endothelial cells have covered the amnion surface and the loss of membrane ruffles results in a smooth endothelial cell monolayer surface. The close association of endothelial cells makes the identification of cellular borders difficult, however, the occasional presence of incompletely attenuated cells provide a point of reference for the evaluation of the cellular nature of this monolayer due to the topology of the underlying Dacron fibers.

The morphology of cells adhered to platelet rich plasma and untreated Dacron was also evaluated after 60 minutes of adherence. Endothelial cell adherence to PRP treated Dacron was observed to involve areas both devoid of cells and areas where cells exhibited endothelial cell characteristic cell to cell interaction. Also of interest is the observed apparent deposition of fibrin on the surface of flattened endothelial cells. Since this fibrin layer was formed prior to seeding, we suggest that endothelial cells are exhibiting the ability to partially migrate under the fibrin lining prior to their complete adherence and flattening. Most important is the common observance of areas which totally lack endothelium and therefore expose the fibrin layer. Finally, adherence of the untreated Dacron surfaces after 60 minutes shows endothelial cells which are wrapped partially around and across individual Dacron fibers in order to resist the forces generated during washing prior to fixation, and during sample preparation for microscopic examination. Patches of multiple endothelial cells were not observed on untreated Dacron surfaces.

Theoretically, vascular graft endothelialization could be produced by low density endothelial cell seeding followed by EC proliferation, high density EC seeding or spontaneous ingrowth of EC onto a surface following implantation. High density EC seeding with establishment of a confluent monolayer at the time of implantation offers the best possibility of a non-thrombogenic graft in the first several weeks following surgery when the risk of thrombosis is present. The aforementioned study was thus untaken to examine whether high density EC seeding was capable of producing a morphologically normal appearing endothelial monolayer within time parameters compatible with an operating room vascular procedure. Experimental conditions were chosen based on our previous observations of EC-graft interactions. However, unlike our previous studies, early passage EC with only 2 prior exposures to trypsin were exclusively used. Two separate methods to study adherence were utilized because we have previously observed that a cell number compatible with a contact-inhibited confluent monolayer (i.e., $10^5$ EC/cm$^2$) does not always correlate with a confluent monolayer on scanning electron microscopy. The radiometric method of quantitating cell adhesion using both tritiated thymidine and Indium was used as an accurate method to measure the number of endothelial cells that are either not adherent, firmly adherent or in the process of attaching to the surface. Using these tools, we have observed that firm adherence takes place within 30 minutes to plasma coated Dacron. In spite of this rapid adherence property, progression to a morphologically normal appearing monolayer is delayed. The endothelial cells at 60 minutes demonstrate few cell to cell interactions, and have a "stellate" morphology rather than a "cobblestone" morphology. Although the non-thrombogenic characteristics of this surface have not been examined, the abnormal morphology suggests that these endothelial cells are not experiencing ideal conditions and may not tolerate the effects of flow. Endothelial cell adherence to the amnion collagen-coated Dacron graft was slower than for the plasma coated, but the attainment of confluence was markedly different. Although the adherence was focal at the early time points by 20 minutes, the endothelial cells were forming many attachment points to the surface and were in the process of flattening and spreading. The process of flattening was maximal by 30 minutes and many cell to cell interactions were present. This resulted in a confluent monolayer on SEM that appeared morphologically similar to native vessel endothelium. This exciting observation suggests that briefly cultured endothelial cells have the capability of becoming a monolayer within a time frame compatible with the surgical dissection time prior to inserting a vascular graft. Thus one may seed a graft at the beginning of the procedure and have a confluent monolayer by the time blood flow is restored.

The adherence study on amnion/collagen coated Dacron reveals that 77% of the seeded endothelial cells adhered to the surface by 30 minutes. This indicates that the majority of briefly cultured EC possess the ability to adhere to the surface and that, most likely, no subgroup of EC with special attachment properties is present or necessary. Since the EC were seeded at a density equivalent to that of a confluent contact-inhibited monolayer $10^5$ EC/cm$^2$), it is also notable that subconfluent attachment (i.e., 77%) still allow the attachment of a morphologically confluent layer. Thus the minimum number of seeded EC necessary to produce complete coverage of a graft without growth may be less than $7.7 \times 10$ EC/cm$^2$.

Confluence in this study is defined as complete EC coverage of the prosthetic surface as seen on scanning electron micrographs. Cell to cell associations appear normal, but further studies with transmission electron micrographs may determine the type of junctions present as well as the type of association between endothelial cells and graft substrate combinations. Substrate is known to have an effect on cell morphology and function and will have to be examined in an experimental setting before concrete conclusions can be drawn. Additionally, more will be learned by studying the use of amnion as a graft substrate. This biologically derived material is not currently available for widespread clinical use. In addition to Type IV/V collagen, the amnion contains the cellular attachment factors of fibronectin and laminin. For large scale production of vascular grafts, it may be desirable to reconstitute a laminate comprised of an intermediate layer of Type I/III collagen and a top surface layer of Type IV/V collagen which mimics the natural basement membrane. If desired, that membrane may further be mimicked by the additions of cellular attachment factors including fibronectin and/or laminin. Whether the basement membrane used is from natural or synthetic origins, it should be noted that such membranes are entirely acellular, may be sterilized by irradiation, and stored and/or shipped for subsequent use. Alternatively, it may be possible to chemically mimic or emulate the desired Type IV/V collagen on the surface of a synthetic prosthesis.

Although the EC monolayer derived from the aforementioned test appears normal morphologically, additional tests (described hereafter) were conducted to investigate whether it possesses other functional characteristics of normal endothelium, particularly with reference to nonthrombogenicity. It is desirable, for example, to show that the monolayer is able to withstand physiological arterial shear stresses and maintain contained adherence. This has been demonstrated not only for the EC-basement membrane adhesion, but also the basement membrane-vascular graft interaction as well as endothelial cell to endothelial cell attachments. It can be concluded from the aforementioned study, however, that the majority of briefly cultured human adult large vessel endothelial cells possess the ability to rapidly adhere within 10 minutes to plasma coated Dacron and within 30 minutes to amnion/collagen-coated Dacron. Adherence to plain Dacron requires longer periods of time before significant adherence has taken place. Although adherence of amnion/collagen-coated Dacron is slower, the net result after 30 minutes is a monolayer of endothelial cells that completely covers the substrate and that appears similar to normal vessel endothelial on scanning electron micrografts. Complete graft coverage does not occur on the plasma coated Dacron or plain Dacron within the 2 hour time frame. The data from the amnion/collagen-coated graft indicates that generation of an endothelial cell monolayer while in the operating room is feasible if a receptive graft-substrate combination is used.

To confirm the functional characteristics of the endothelial cell monolayer created by high density seeding on amnion, and to demonstrate that the procedure is effective when using endothelial cells of microvascular origin, the preparation of an amnion coated graft surface was accomplished as described above, but using a Dacron graft surface which had first been pretreated using a glow discharge plasma cleaner to prepare that surface for collagen coating. This procedure involves the placement of the prosthesis in a Harrick plasma cleaner for 5 minutes. The glow discharge plasma created in this device etches the graft surface and creates a stronger association between the collagen and graft.

Feasibility of the procedure was demonstrated using a dog model. An amnion coated Dacron graft was seeded with dog microvessel endothelial cells and the seeded graft was surgically implanted in the vena cava of a dog. After two days, the graft was removed and the surface examined by scanning electron microscopy. This examination indicated that the surface is covered by a cellular layer which inhibits association of blood cells (white cells and platelets). This test failed to reveal any indication that the subject graft would not have indefinite patency. A control surface placed in an artery, on the other hand, exhibited the normal thrombogenic characteristic of an untreated polymer when exposed to blood.

As seen from the above, the present application discloses a novel method of treating an implant intended for implantation in a human patient, comprising providing a synthetic substrate material and treating that material with Type IV/V collagen to improve human endothelial cell adhesion, proliferation and morphology thereon. In the preferred embodiment, the Type IV/V collagen is bound as a surface layer for receiving endothelial cells. Preferably, the Type IV/V collagen surface layer is applied as a laminate having a Type I/III collagen underlayer adherent to it. In the preferred embodiment, the aforementioned collagen laminate is derived from human chorioallantoic membrane, and comprises acellular human amnion. This collagen laminate (amnion) is applied to a substrate having a bound interstitial collagen base layer formed thereon. The base layer is adhered to the substrate through the use of a cross linking agent, such as glutaraldehyde, which further activates the surface of the base layer to permit covalent binding of the collagen laminate to that base layer. The linking agent is then safely deactivated using an amine, amino acid or peptide with an aldehyde active amine group, such as lysine, which is soluble in buffered saline. Following washing to remove the deactivating agent and residual linking agent, the graft is ready to receive high density seeding of microvessel endothelial cells. These microvessel endothelial cells are seeded at a density of at least $5 \times 10^4$, preferably at least $7.7 \times 10^4$, cells per cm$^2$ to form a confluent monolayer on the graft surface within two hours from the time of seeding. It is currently preferred to seed in range of 1-3, or about $2 \times 10^5$ cells per cm$^2$. While microvessel endothelial cells are preferred due to their uncultured, autologous nature, it is within the scope of the present invention to use human adult endothelial cells which have been briefly cultured for two or less passages, in those instances where such cells are readily available. Since the resulting graft possesses an endothelial lining of autologous endothelial cells, its patency, particularly during the critical early period after implantation, may be expected to be markedly improved. Use of the subject grafts for venous implants, and in vessels having diameters of 4 mm or less (small caliber grafts), where patency rates have otherwise been disappointingly low is thus anticipated.

"Dacron" is a trademark of E. I. duPont de Nemours and Company of Wilmington, Del., which is used to identify a particular polyethylene terephthalate polyester which is a condensation product of methyl terephthalate and ethylene glycol. Those of ordinary skill in the art will further recognize that various departures can be made from the methods and procedures described herein without departing from the scope of the present invention, which is defined more particularly in the claims appended hereto.

As used herein the term "cobblestone" refers to both the typical symmetrical endothelial cell-cell morphology exhibited, for example, by bovine aortic endothelial cells in culture (sometimes referred to in the art as "true cobblestone") as well as cellular morphologies wherein the cells are generally round but have some projections or other asymmetrical portions. In particular, as used in this application the term cobblestone refers to populations of endothelial cells which form tight cell to cell associations, i.e., those which attenuate to maximally cover the underlying surface.

What is claimed:

1. A method for treating an intravascular implant prior to implantation in a human patient comprising the steps of:
    (a) treating an implant comprising a synthetic substrate material by subjecting the implant to glow discharge etching for a period of time sufficient to improve the adherence of microvascular endothelial cells; and
    (b) applying freshly isolated microvascular endothelial cells obtained from tissue having a high content of microvascular endothelial cells to provide about 50% or more confluence of said cells on the surface of said implant.

2. The method of claim 1 wherein said synthetic substrate is selected to a polyester material.

3. The method of claim 2 wherein said polyester material is a fibrous material.

4. The method of claim 3 wherein said polyester material is a woven material.

5. The method of claim 1 wherein said endothelial cells are isolated from fat tissue.

6. The method of claim 5 wherein said fat tissue is subcutaneous fat.

7. The method of claim 5 wherein said fat tissue is perinephric fat.

8. The method of claim 5 wherein said fat tissue is omentum.

9. The method of claim 5 wherein said fat tissue is intrathoracic fat.

10. The method of claim 5 wherein said fat tissue is intraperitoneal fat.

* * * * *

UNITED STATES PATENT AND TRADEMARK OFFICE
CERTIFICATE OF CORRECTION

PATENT NO. : 5,131,907

DATED : July 21, 1992

INVENTOR(S) : Williams et al.

It is certified that error appears in the above-identified patent and that said Letters Patent is hereby corrected as shown below:

Column 14, Line 36, "$10^8$" should be "$10^6$".

Column 20, Line 61, after "were" add --performed--.

Column 21, Line 56, change "gradel" to --graded--.

Signed and Sealed this

Twenty-fifth Day of October, 1994

Attest:

BRUCE LEHMAN

Attesting Officer

Commissioner of Patents and Trademarks